(12) United States Patent
Kovacs, Jr. et al.

(10) Patent No.: US 8,355,548 B2
(45) Date of Patent: Jan. 15, 2013

(54) LOAD INDEPENDENT INDEX OF DIASTOLIC FUNCTION

(75) Inventors: Sandor J. Kovacs, Jr., St. Louis, MO (US); Leonid Shmuylovich, St. Louis, MO (US); Charles Sangwoo Chung, Tucson, AZ (US)

(73) Assignee: Washington University, St. Louis, MO (US)

( * ) Notice: Subject to any disclaimer, the term of this patent is extended or adjusted under 35 U.S.C. 154(b) by 1161 days.

(21) Appl. No.: 12/088,805

(22) PCT Filed: Sep. 29, 2006

(86) PCT No.: PCT/US2006/038647
§ 371 (c)(1),
(2), (4) Date: Sep. 11, 2008

(87) PCT Pub. No.: WO2007/038798
PCT Pub. Date: Apr. 5, 2007

(65) Prior Publication Data
US 2009/0043213 A1  Feb. 12, 2009

Related U.S. Application Data

(60) Provisional application No. 60/721,739, filed on Sep. 29, 2005.

(51) Int. Cl.
*G06K 9/00* (2006.01)

(52) U.S. Cl. .................................. 382/128

(58) Field of Classification Search .................. None
See application file for complete search history.

(56) References Cited

U.S. PATENT DOCUMENTS

| | | | |
|---|---|---|---|
| 6,517,485 B2 * | 2/2003 | Torp et al. | 600/438 |
| 2004/0193035 A1 * | 9/2004 | Gharib | 600/407 |
| 2006/0282125 A1 | 12/2006 | McConnell | |

FOREIGN PATENT DOCUMENTS

RU  2088146 C1 *  8/1997

OTHER PUBLICATIONS

Enghish machine translation of RU 2088146 C1, Method to Predict Diastolic Failure of Left Ventricle in Patients with Hyperthrophic Cardiomyopathy, to inventors Alekseevich et al, published on Aug. 27, 1997, 9 pages total.*

Sztajzel J., et al., Effect of altered loading conditions during haemodialysis on left ventricular filling pattern, Eur. Heart J., 1993, p. 655-61, vol. 14(5).

Takahashi T., et al., Doppler echocardiographic-determined changes in left ventricular diastolic filling flow velocity during the lower body positive and negative pressure method, Am. J. Cardiol., 1990, p. 237-41, vol. 65(3).

Tanabe M., et al., Change in filling pattern with preload reduction reflects left ventricular relaxation, Intern. J. Cardiology, 2005, p. 67-72, vol. 98.

(Continued)

*Primary Examiner* — Brian P Werner
(74) *Attorney, Agent, or Firm* — Armstrong Teasdale LLP

(57) ABSTRACT

Methods and related apparatus and systems for determining a load-independent index of diastolic function in the heart are described.

19 Claims, 17 Drawing Sheets

OTHER PUBLICATIONS

Thomas J.D., et al., Analysis of the Early Transmitral Doppler Velocity Curve: Effect of Primary Physiologic Changes and Compensatory Preload Adjustment, JACC, 1990, p. 644-55, vol. 16(3).
Triulzi M.O., et al., Effects of preload reduction on mitral flow velocity pattern in normal subjects, Am. J. Cardiol., 1990, p. 995-1001, vol. 66(12).
Vanoverschelde J.L., et al., Noninvasive estimation of pulmonary arterial wedge pressure with Doppler transmitral flow velocity pattern in patients with known heart disease, Am. J. Cardiol., 1995, p. 383-9, vol. 75.
Voller H., et al., Doppler echocardiography measurement of diastolic filling parameters in acute changes of pre- and afterload in healthy probands, Z. Kardiol., 1992, p. 687-94, vol. 81(12).
Yalcin F., et al., Is Doppler tissue velocity during early left ventricular filling preload independent?, Heart, 2002, p. 336-39, vol. 87.
Yamamoto K., et al., Determination of left ventricular filling pressure by Doppler echocardiography in patients with coronary artery disease: critical role of left ventricular systolic function, J. Am. Coll. Cardiol., 1997, p. 1819-26, vol. 30.
Yamamoto K., et al., Peak early diastolic filling velocity may decrease with preload augmentation: effect of concomitant increase in the rate of left atrial pressure drop in early diastole, J. Am. Soc. Echocardiogr., 1993, p. 245-54, vol. 6(3 Pt 1).
Voller H., et al., Acute alterations of pre- and afterload: Are Doppler-derived diastolic filling patterns able to differentiate the loading conditions?, Int. J. Cardiac Imag., 1993, p. 231-240, vol. 9.
International Search Report in the related application PCT/US06/38647, issued on May 14, 2007.
Appleton C.P., et al., Doppler Evaluation of Left and Right Ventricular Diastolic Function: a Technical Guide for Obtaining Optimal Flow Velocity Recordings, J. Am. Soc. Echocardiogr, 1997, p. 271-92, vol. 10(3).
Appleton C.P., et al., Estimation of left ventricular filling pressures using two-dimensional and Doppler echocardiography in adult patients with cardiac disease. Additional value of analyzing left atrial size, left atrial ejection fraction and the difference in duration of pulmonary venous and mitral flow velocity at atrial contraction, J. Am. Coll. Cardiol., 1993, p. 1972-82, vol. 22.
Appleton C.P., et al., The Echo-Doppler Evaluation of Left Ventricular Diastolic Function: a Current Perspective, In: Diastolic Function and Dysfunction, Kovacs S.J. ed., Philadelphia, PA, Saunders, 2000, p. 513-46.
Bauman L., et al., The peak atrioventricular pressure gradient to transmitral flow relation: kinematic model prediction with in-vivo validation, J. Am. Soc. Echocardiogr., 2004, p. 839-44, vol. 17(8).
Dagdelen S., et al., Estimation of left ventricular end-diastolic pressure by color M-mode Doppler echocardiography and tissue Doppler imaging, J. Am. Soc. Echocardiogr., 2001, p. 951-8, vol. 14.
Dent C.L., et al., Echocardiographic characterization of fundamental mechanisms of abnormal diastolic filling in diabetic rats with a parameterized diastolic filling formalism, J. Am. Soc. Echocardiogr, 2001, p. 1661-72, vol. 14(12).
Downes T.R., et al., Effect of Alteration in Loading Conditions on Both Normal and Abnormal Patterns of Left Ventricular Filling in Healthy Individuals, Am. J. Cardiology, 1990, p. 377-82, vol. 65.
Garcia M.J., et al., An index of early lefty ventricular filling that combined with pulsed Doppler peak E velocity may estimate capillary wedge pressure, J. Am. Coll. Cardiol., 1997, p. 448-54, vol. 29.
Garcia M.J., et al., Color M-mode Doppler flow propagation velocity is a preload insensitive index of left ventricular relaxation: animal and human validation, J. Am. Coll. Cardiol., 2000, p. 201-8, vol. 35(1).
Garcia M.J., et al., Color M-mode Doppler flow propagation velocity is a relatively preload-independent index of left ventricular filling, J. Am. Soc. Echocardiogr., 1999, p. 129-37, vol. 12(2).
Granzier H.L. and Labeit S., The giant protein titin: a major player in myocardial mechanics, signaling, and disease, Circ. Res., 2004, p. 284-95, vol. 94(3).
Hall A.F. and Kovacs S.J., Automated method for characterization of diastolic transmitral Doppler velocity contours: Early rapid filling, Ultrasound in Medicine & Biology, 1994, p. 107-16, vol. 20.

Hall A.F. and Kovacs S.J., Automated Quantification of Diastolic Filling Parameters from Cardiac Doppler Ultrasound, Proceedings IEEE Ultrasonics Symposium, 1992, p. 1125-28.
Hall A.F. and Kovacs S.J., Model-Based Image Processing of Doppler Velocity Profiles: Toward Automation, IEEE Ultrasonics, Ferroelectrics and Frequency Control Conference Proceedings, 1995.
Hall A.F. and Kovacs S.J., Processing parameter effects on the robustness of the solution to the "Inverse Problem" of diastole from Doppler echocardiographic data, 15th Annual International Conference, IEEE Engineering in Medicine & Biology Society, 1993, p. 1385-87.
Hall A.F., et al., Automated method for characterization of diastolic transmitral Doppler velocity contours: Late atrial filling, Ultrasound in Medicine & Biology, 1994, p. 859-69, vol. 20.
Hurrell D.G., et al., Utility of preload alteration in assessment of left ventricular filling pressure by Doppler echocardiography: a simultaneous catheterization and Doppler echocardiographic study, J. Am. Coll. Cardiol., 1997, p. 459-67, vol. 30(2).
Kidawa M., et al., Comparative value of tissue Doppler imaging and m-mode color Doppler mitral flow propagation velocity for the evaluation of left ventricular filling pressure, Chest, 2005, p. 2544-50, vol. 128.
Kmetzo J.J., et al., Effect of postural changes and isometric exercise on Doppler derived measurements of diastolic function in normal subjects, Chest, 1991, p. 357-63, vol. 100(2).
Kovacs S.J., et al., Can Transmitral Doppler E-waves Differentiate Hypertensive Hearts From Normal?, Hypertension, 1997, p. 788-95, vol. 30(4).
Kovacs S.J., et al., Evaluation of Diastolic Function with Doppler Echocardiography: The PDF Formalism, American Journal of Physiology, 1987, p. H178-87, vol. 252(1 Pt 2).
Kovacs S.J., et al., Modeling cardiac fluid dynamics and diastolic function, Philosophical Transactions of the Royal Society, 2001, p. 1299-1314, vol. 359.
Kovacs S.J., et al., Modeling of Diastole, Cardiology Clinics of North America, 2000, p. 459-87, vol. 18(3).
Kuecherer H.F., et al., Determination of left ventricular filling parameters by pulsed Doppler echocardiography: a noninvasive method to predict high filling pressures in patients with coronary artery disease, Am. Heart J., 1988, p. 1017-21, vol. 116.
Kuecherer H.F., et al., Estimation of mean left atrial pressure from transesophageal pulsed Doppler echocardiography of pulmonary venous flow, Circulation, 1990, p. 1127-39, vol. 82.
Lin S.K., et al., Color M-Mode Flow Propagation Velocity: Is It Really Preload Independent?, Echocardiography, 2005, p. 626-64, vol. 22(8).
Lisauskas J.B., et al. Chamber properties from transmitral flow: prediction of average and passive left ventricular diastolic stiffness, J. Appl. Physiol., 2001, p. 154-62, vol. 91(1).
Lisauskas J.B., et al., The relation of the peak doppler E-wave to peak mitral annulus velocity ratio to diastolic function, Ultrasound in Medicine & Biology, 2001, p. 499-507, vol. 27(4).
Masuyama T., et al., Effects of nitroprusside on transmitral flow velocity patterns in extreme heart failure: a combined hemodynamic and Doppler echocardiographic study of varying loading conditions, J. Am. Coll. Cardiol., 1990, p. 1175-85, vol. 16(5).
Mulvagh S., et al., Estimation of left ventricular end-diastolic pressure from Doppler transmitral flow velocity in cardiac patients independent of systolic performance, J. Am. Coll. Cardiol., 1992, p. 112-9, vol. 20.
Nagueh S.F., et al., Doppler estimation of left ventricular filling pressure in sinus tachycardia. A new application of tissue Doppler imaging, Circulation, 1998, p. 1644-50, vol. 98.
Nagueh S.F., et al., Doppler estimation of left ventricular filling pressures in patients with hypertrophic cardiomyopathy, Circulation, 1999, p. 254-61, vol. 99.
Nagueh S.F., et al., Doppler tissue imaging: a noninvasive technique for evaluation of left ventricular relaxation and estimation of filling pressures, J. Am. Coll. Cardiol., 1997, p. 1527-33, vol. 30.
Nishimura R.A., et al., Noninvasive Doppler echocardiographic evaluation of left ventricular filling pressures in patients with cardiomyopathies: a simultaneous Doppler echocardiographic and cardiac catheterization study, J. Am. Coll. Cardiol., 1996, p. 1226-33, vol. 28.

Ommen S.R., et al., Clinical utility of Doppler echocardiography and tissue Doppler imaging in the estimation of left ventricular filling pressures: A comparative simultaneous Doppler-catheterization study, Circulation, 2000, p. 1788-94, vol. 102.

Oommen B., et al., Modeling Time Varying Elastance: The Meaning of Load-Independence, Cardiovascular Engineering, 2003, p. 123-130, vol. 3(4).

Paelinck B.P., et al., Effects of Postural Changes on Cardiac Function in Healthy Subjects, Eur. J. Echocardiography, 2003, p. 196-201, vol. 4.

Pela G., et al., Effects of the reduction of preload on left and right ventricular myocardial velocities analyzed by Doppler tissue echocardiography in healthy subjects, Eur. J. Echocardiogr., 2004, p. 262-71, vol. 5(4).

Pepi M., et al., Diastolic Ventricular Interaction in Normal and Dilated Heart During Head-Up Tilting, Clin. Cardiology, 2000, p. 665-72, vol. 23.

Plotnick G.D., et al., Effect of autonomic blockade, postural changes and isometric exercise on Doppler indexes of diastolic left ventricular function, Am. J. Cardiol., 1991, p. 1284-90, vol. 67(15).

Pozzoli M., et al., Doppler echocardiography reliably predicts pulmonary artery wedge pressure in patients with chronic heart failure with and without mitral regurgitation, J. Am. Coll. Cardiol., 1996, p. 883-93, vol. 27.

Riordan M.M., et al., Diabetes and Diastolic Dysfunction: Stiffness and relaxation from transmitral flow, Ultrasound in Medicine & Biology, 2005, p. 1589-96, vol. 31(12).

Robinson D.F., et al., The heart as a suction pump, Sci. Am., 1986, p. 84-91, vol. 254.

Sagawa K., et al., End-systolic pressure-volume ratio: a new index of ventricular contractility, Am. J. Cardiol., 1977, p. 748-53, vol. 40(5).

Schwengel R.H., et al., Abnormal Valsalva blood pressure response in dilated cardiomyopathy: association with "pseudonormalization" of echocardiographic Doppler transmitral filling velocity pattern, Am. Heart J., 1993, p. 1182-6, vol. 126(5).

Shmuylovich L. and Kovacs S.J., A load independent index of diastolic filling: model-based derivation with in-vivo validation in control and diastolic dysfunction subjects, J. Appl. Physiol., 2006, p. 92-101, vol. 101(1).

Stoddard M.F., et al., Influence of alteration in preload on the pattern of left ventricular diastolic filling as assessed by Doppler echocardiography in humans, Circulation, 1989, p. 1226-36, vol. 79(6).

Stork T.V., et al., Noninvasive measurement of left ventricular filling pressures by means of transmitral pulsed Doppler ultrasound, Am. J. Cardiol., 1989, p. 655-60, vol. 64.

Suga H., et al., Load Independence of the Instantaneous Pressure-Volume Ratio of the Canine Left Ventricle and Effects of Epinephrine and Heart Rate on the Ratio, Circ. Res., 1973, p. 314-22, vol. 32.

Suzuki T., et al., Influence of postural change on transmitral flow velocity profile assessed by pulsed Doppler echocardiography in normal individuals and in patients with myocardial infarction, Am. Heart J., 1990, p. 110-5, vol. 120(1).

* cited by examiner

LOAD INDEPENDENT INDEX OF DIASTOLIC FUNCTION

CROSS-REFERENCE TO RELATED APPLICATIONS

This application claims priority from U.S. Provisional Application Ser. No. 60/721,739 filed on Sep. 29, 2005, and from PCT Application No. PCT/US2006/038647, filed on Sep. 29, 2006, which are both incorporated herein by reference in their entirety.

STATEMENT REGARDING FEDERALLY SPONSORED RESEARCH OR DEVELOPMENT

This invention was made in part with the support of NIH grant K-24 KL-04023-05. The government has certain rights in this invention.

BACKGROUND OF THE INVENTION

This invention relates generally to medical methods and devices and, more particularly, relates to methods and apparatus for analysis of diastolic function.

Cardiologists examining heart function face a challenging analytical task. In theory, pressure and volume data from the heart chambers should provide important information regarding heart muscle function. However, analysis of pressure-volume data from the heart is complex because pressures and volumes both depend on simultaneously variable factors such as preload, afterload, and contractility.

Maximum elastance ($E_{max}$), or the slope of the end-systolic pressure volume relation (ESPVR), serves as a physiologically useful, load independent index of systolic function. (H. Suga et al., "Load independence of the instantaneous pressure-volume ratio of the canine left ventricle and effects of epinephrine and heart rate on the ratio", Circ Res 32: 314 (1973); K. Sugawa et al., "End-systolic pressure-volume ratio: a new index of ventricular contractility", Am J Cardiol 40: 748 (1977)) Modeling the ventricle as a time varying elastance has permitted the derivation and validation of $E_{max}$, which has thereby provided a characterization of left ventricle (LV) chamber contractility. Such an approach is based on the finding that that the instantaneous pressure to volume ratio in the heart, where the volume is measured relative to a "lax" volume $V_o$, defines a time-varying elastance. The time-varying elastance attains the same maximum value at a fixed contractile state regardless of changes in load. Thus $E_{max}$ is known as a valid load-independent index of systolic function. Additional conceptual validation of $E_{max}$ as a load independent index of systolic function has been achieved using a kinematic, forced harmonic oscillator-based argument showing that the slope of the maximum force-displacement relationship (ESPVR analog) depends only on the intrinsic parameters of the oscillator rather than the initial conditions (load). (B. Oommen et al., "Modeling Time Varying Elastance: The Meaning of "Load-Independence"", Cardiovascular Engineering 3(4): 123-130 (2003)).

$E_{max}$ has been found to be well approximated by the ESPVR. Furthermore, enhanced contractile states, achieved through epinephrine stimulation, generate higher maximum elastance values. Thus, $E_{max}$ is an accepted, load-independent measure of contractility. Although it is known that the global end-systolic P-V (elastance) relation is curvilinear, a linear approximation is justified because the amount of nonlinearity in the physiologic range is modest.

While $E_{max}$ is a chamber property which is uncoupled from the effects of load on systolic function, no equivalent load-independent property or measure has been predicted to exist, nor has one been experimentally (empirically) discovered, for diastole. Thus, in contrast to the 'load-independent index of systolic function' problem, the 'load-independent index of diastolic function' problem remains to be solved. For example, echocardiographic global diastolic function assessment utilizes a broad array of transmitral flow or tissue motion-based indices that are known to be load-dependent. Conventional approaches to diastolic function (DF) index determination have been primarily correlative, and have not yielded a load independent index of DF (LIIDF).

Echocardiography is a preferred and accepted noninvasive method for DF assessment. Doppler echocardiography derived indices have been used to characterize DF in numerous cardiac disorders including heart failure, myocardial infarction, reversible myocardial ischemia, hypertrophic cardiomyopathy, and hypertension (S. J. Kovács et al., "Can Transmitral Doppler E-waves Differentiate Hypertensive Hearts From Normal?" Hypertension 30: 788-795 (1997)). Pulsed wave Doppler echocardiography is used for transmitral flow assessment. In current practice, most DF indices are derived by visual inspection of transmitral E- and A-wave shape. There are dozens of shape-derived indices, the most common ones include: the peak velocity of the E-wave ($E_{peak}$), the duration of the E-wave ($E_{dur}$), the acceleration and deceleration times of the E-wave (AT and DT) and the area under the E-wave (velocity-time integral, VTI). Additional indices include the peak velocity of the A wave ($A_{peak}$) and the ratio of the E and A peak velocities (E/A). However, most of the clinically relevant Doppler derived DF indices have proven to be load dependent. (S. J. Kovács et al., "Modeling of Diastole", Cardiology Clinics of North America 18(3): 459-490 (2000); S. J. Kovács et al., "Modeling cardiac fluid dynamics and diastolic function", Philosophical Transactions of the Royal Society (A)359: 1299-1314 (2001)). To date, E/E', (the ratio of $E_{peak}$ to the mitral annular peak velocity E'), measured by Doppler tissue imaging, is the sole DF index for which its relation to LVEDP, i.e. its load dependence, has been characterized based on first principles (J. B. Lisauskas et al., "The Relation of the Peak Doppler E-wave to Peak Mitral Annulus Velocity Ratio to Diastolic Function", Ultrasound in Medicine and Biology 27(4): 499-507 (2001)).

In addition, non-invasive indexes derived from Doppler echocardiography have been used to estimate invasively derived left ventricular pressures. Left ventricular pressures, such as the minimum diastolic (filling phase) pressure ($LVP_{min}$), the end-diastolic pressure (LVEDP), the diastasis or pre-A wave pressure, as well as the average filling pressure, are invasive measures that are employed in clinical practice to aid in patient management and diagnosis. Swan-Ganz catheter pulmonary capillary wedge pressure (PCWP) is also an important invasive measure that is routinely employed clinically as a surrogate for the atrial pressure and used for diagnosis and monitoring. Gold standard determination of these mentioned pressures requires invasive catheterization, and numerous studies, over the last two decades, have attempted to estimate invasive pressures with the aid of Doppler echocardiography. See, e.g., Kuecherer HF et al. "Determination of left ventricular filling parameters by pulsed Doppler echocardiography: a noninvasive method to predict high filling pressures in patients with coronary artery disease." American Heart Journal 116(4): 1017-1021 (1988). Kidawa M et al. "Comparative value of tissue Doppler imaging and m-mode color Doppler mitral flow propagation velocity for the evaluation of left ventricular filling pressure." Chest 128

(4):2544-2550 (2005)). E/E', $E_{peak}$, $E_{peak}/A_{peak}$, $A_{dur}$, velocity of propagation ($V_p$), $E_{peak}/V_p$, DT, isovolumic relaxation time (IVRT), and $A_{dur}$-$Ar_{dur}$ have all been tested as noninvasive estimates of LVEDP. While each index has shown marginal success in specific homogeneous patient groups, all non-invasive indexes, with the exception of E/E' fail to correctly predict invasive pressures in patients with normal systolic function. This is a significant limitation because up to 50% of patients with heart failure suffer from diastolic heart failure with normal systolic function.

Accordingly, there remains a need for methods and related systems that provide a load-independent index of diastolic function, as well as a need for methods and related systems that provide a non-invasive measure of left ventricular operating pressures.

BRIEF SUMMARY OF THE INVENTION

The present invention is based in part on the discovery that a load-independent index of diastolic function (LIIDF) can be obtained by: 1) applying a mathematical model for E-wave contour analysis (the PDF formalism) to E-waves obtained at different loads, and by using the model derived parameters ($x_o$, c, k) to determine maximum driving force ($kx_o$) and peak resistive force ($cE_{peak}$) in humans, and that the $kx_o$ vs $cE_{peak}$ relationship is linear (i.e. has constant slope) and is therefore load-independent. The intercept of the $kx_o$ vs $cE_{peak}$ relationship provides a non-invasive estimate to left ventricular operating pressures (LVEDP, PCWP, etc.); 2) applying a non-PDF model-based approach, using a triangle approximation for E-wave shape, applied to E-waves obtained at different loads, to determine the value of the E-wave acceleration time (AT), a value for the E-wave deceleration time (DT), and a value for the peak amplitude of the E-wave ($E_{peak}$). These values determined by approximating the E-wave as a triangle are used to plot the $$E_{peak}/AT \text{ vs. } \frac{E_{peak}}{AT} \frac{DT^2 - AT^2}{(DT^2 - AT^2 + AT \cdot DT)} \text{ relationship}$$

slope of which also provides the analogous LIIDF; 3) applying a non-PDF model-based approach, applied to E-waves obtained at different loads, to determine a value for acceleration time (AT), a value for the E-wave deceleration time (DT), a value for the peak amplitude ($E_{peak}$), a value for the amplitude at a time of 2AT ($E_{2AT}$), and a value for the amplitude at a time of AT/2 ($E_{AT/2}$). These values determined by direct measurements of the E-wave contours obtained at different loads are used to plot the $$2E_{AT/2}/AT \text{ vs. } \frac{4E_{AT} \cdot DT}{(DT^2 - AT^2 + AT \cdot DT)} \frac{E_{2AT}}{E_{peak} - E_{2AT}},$$

slope of which also provides the analogous LIIDF, and the intercept (B) of which provides a non-invasive estimate for left ventricular pressures (LVEDP, PCWP, etc.). The LIIDF (slope) and vertical intercept (B) can be obtained using data obtained from any invasive or noninvasive imaging modality that provides ventricular volume as a function of time during the cardiac cycle and/or its rate of change.

Accordingly, in one embodiment there is provided a method for obtaining an index of cardiac function comprising obtaining imaging data in at least 2 different load states, that is representative of diastolic transmitral flow velocity in a subject, and analyzing the imaging data to determine a load-independent index of diastolic function in the subject. Analyzing the imaging data comprises, in one embodiment, identifying E-waves in the imaging data from different load states, determining values of peak-resistive force ($cE_{peak}$) from the set of E-waves, determining values of peak-driving force ($kx_o$) from the set of E-waves, determining a linear function describing a relationship of maximum driving force versus peak-resistive force for the set of E-waves, and determining the slope and vertical intercept of the function of maximum driving force versus peak-resistive force. In one embodiment of the method, the imaging data is obtained using a noninvasive imaging modality. In one embodiment, the imaging data is obtained using an echocardiogram.

In another embodiment, analyzing the imaging data comprises identifying a set of E-waves in the imaging data from several beats at varying loads, approximating the E-waves as triangles, determining a value for the acceleration time of the E-wave (AT) from each E-wave, determining a value for a deceleration time (DT) from each E-wave, determining the peak amplitude of each E-wave ($E_{peak}$), calculating the $E_{peak}$/AT ratio for each E-wave, calculating the peak viscous/resistive force geometric equivalent $$\left( \frac{E_{peak}}{AT} \frac{DT^2 - AT^2}{(DT^2 - AT^2 + AT \cdot DT)} \right)$$

for each E-wave, determining the linear function describing a relationship of the $E_{peak}$/AT ratio to the peak viscous/resistive force geometric equivalent $$\frac{E_{peak}}{AT} \frac{DT^2 - AT^2}{(DT^2 - AT^2 + AT \cdot DT)},$$

and determining a slope and vertical intercept of the function of maximum driving force versus peak resistive force. In one embodiment of the method, the imaging data is obtained using a non-invasive imaging modality. In one embodiment, the imaging data is obtained using an echocardiogram.

In another embodiment, analyzing the imaging data comprises identifying a set of E-waves in the imaging data from several beats at varying loads, determining the initial point, peak point, and end point of each E-wave, determining a value for the acceleration time of the E-wave (AT) from each E-wave, determining a value for a deceleration time (DT) from each E-wave, determining the peak amplitude of each E-wave ($E_{peak}$), determining the amplitude of each E-wave at a time t=2AT ($E_{2AT}$), determining the amplitude of each E-wave at a time t=AT/2 ($E_{AT/2}$), calculating the maximum driving force geometric equivalent $2E_{AT/2}$/AT ratio for each E-wave (or equivalent estimate of the maximum upward slope of the E-wave beginning on the initial defined point), calculating the peak viscous/resistive force geometric equivalent $$\left( \frac{4E_{AT} \cdot DT}{(DT^2 - AT^2 + AT \cdot DT)} \frac{E_{2AT}}{E_{peak} - E_{2AT}} \right)$$

for each E-wave, determining the linear function describing a relationship of the $2E_{AT/2}/AT$ ratio to the peak viscous/resistive force geometric equivalent $$\frac{4E_{\frac{AT}{2}} \cdot DT}{(DT^2 - AT^2 + AT \cdot DT)} \frac{E_{2AT}}{E_{peak} - E_{2AT}},$$

and determining a slope and vertical intercept of the function of maximum driving force versus peak resistive force. In one embodiment of the method, the imaging data is obtained using a non-invasive imaging modality. In one embodiment, the imaging data is obtained using an echocardiogram.

In another embodiment, a method for measuring cardiac function comprises determining a value of a spring constant k of a spring representative of chamber recoil; determining a value of a chamber viscoelastic damping constant c; determining a value of an initial displacement of the spring $x_o$; and using the value of the spring constant k, the value of the damping constant c, and the value of the initial displacement of the spring $x_o$ to calculate a load independent index of diastolic function. In one embodiment, the spring constant k, the damping constant c, and the initial displacement of the spring $x_o$ are determined from E-waves obtained at different load states identified in imaging data representative of diastolic transmitral blood flow velocity or of tissue motion. In one embodiment of the method, the imaging data is obtained using a non-invasive imaging modality. In one embodiment, the imaging data is obtained using an echocardiogram.

In another embodiment, there is provided a system for analyzing cardiac function in a subject, the system comprising a computer usable medium comprising computer readable code embodied therein, the computer readable code configured to receive an input of imaging data representative of diastolic transmitral flow or tissue motion velocity in a subject, the computer readable code further configured to generate a load-independent index of diastolic function in the subject from the imaging data. In one embodiment the system further comprises a computer configured to operate using the computer usable medium, and display apparatus operatively coupled to the computer, the display apparatus for displaying the imaging data and the load-independent index of diastolic function. The system in another embodiment includes computer readable code comprising computer readable code configured to identify a set of E-waves in the imaging data representative of diastolic transmitral flow at different load states, computer readable code configured to determine a value of peak resistive force ($cE_{peak}$) from all the E-waves, computer readable code configured to determine a value of peak-driving force ($kx_o$) from all the E-wave, computer readable code configured to generate a linear function describing a relationship of maximum driving force versus peak resistive force for the set of E-waves, and computer readable code configured to determine a slope and vertical intercept of the function of maximum driving force versus peak resistive force.

In another embodiment there is provided apparatus for displaying indices of cardiac function in a subject, the apparatus comprising a computer usable medium comprising computer readable code embodied therein, the computer readable code configured to receive an input of imaging data (acquired in at least 2 different load states) representative of diastolic transmitral flow velocity or tissue motion in a subject, the computer readable code further configured to generate a load-independent index of diastolic function in the subject from the imaging data, and visual display apparatus operatively coupled to the computer usable medium, the visual display apparatus configured to display the imaging data and the load independent index of diastolic function.

In another embodiment there is provided a diagnostic system for analyzing cardiac function in a subject, the system comprising a computer processor, the computer processor configured with computer readable instructions comprising instructions for receiving and storing an input of imaging data representative of diastolic transmitral flow velocities at various load states in a subject; and instructions for generating a load independent index of diastolic function in the subject from the imaging data. In one embodiment the diagnostic system includes computer readable instructions further comprising instructions for identifying a set of E-waves in the imaging data, instructions for determining a value of peak resistive force ($cE_{peak}$) from each of the E-waves, instructions for determining a value of peak-driving force ($kx_o$) from each of the E-waves, instructions for generating a linear function describing a relationship of maximum driving force versus peak resistive force, and instructions for determining a slope and vertical intercept of the function of maximum driving force versus peak resistive force.

In another embodiment the diagnostic system includes computer readable instructions further comprising instructions for identifying a set of E-waves in the imaging data acquired at different load states, approximating the shape of the E-waves as triangles, or as mathematically smoothed contours closely approximating the shape of the E-wave, instructions for determining a value for acceleration time of the E-wave (AT) from each E-wave, instructions for determining a value for deceleration time of the E-wave (DT) from each E-wave, instructions for determining a value for peak amplitude of the E-wave ($E_{peak}$) from each E-wave, instructions for determining a value for the geometric maximum driving force (the $E_{peak}/AT$ ratio) from each E-wave, instruction for determining a value for the geometric peak viscous/resistive force $$\left(\text{given by } \frac{E_{peak}}{AT} \frac{DT^2 - AT^2}{(DT^2 - AT^2 + AT \cdot DT)}\right)$$

from each E-wave, instructions for generating a linear function describing a relationship of the geometric maximum driving force to the geometric peak viscous/resistive force, and instructions for determining a slope and vertical intercept of the function of geometric maximum driving force versus geometric peak resistive/viscous force.

In another embodiment the diagnostic system includes computer readable instructions further comprising instructions for identifying a set of E-waves in the imaging data acquired at different load states, instruction for determining the initial, peak and end points of each E-wave, instructions for determining a value for acceleration time of the E-wave (AT) from each E-wave, instructions for determining a value for deceleration time of the E-wave (DT) from each E-wave, instructions for determining a value for peak amplitude of the E-wave ($E_{peak}$) from the E-wave, instructions for determining a values for the amplitude of the E-wave at a time t=2AT ($E_{2AT}$) for each E-wave, instruction for determining a value for the amplitude of the E-wave at a time t=AT/2 ($E_{AT/2}$) for each E-wave, instructions for determining a value for the geometric maximum driving force (the maximum initial upslope of the E-wave approximated by $2E_{AT/2}/AT$ or other more exact method) for each E-wave, instruction for determining a value for the geometric peak viscous/resistive force $$\left(\text{given by } \frac{4E_{AT \over 2} \cdot DT}{(DT^2 - AT^2 + AT \cdot DT)} \frac{E_{2AT}}{E_{peak} - E_{2AT}}\right),$$

instructions for generating a linear function describing a relationship of the geometric maximum driving force to the geometric peak viscous/resistive force, and instructions for determining a slope and vertical intercept of the function of geometric maximum driving force versus geometric peak resistive/viscous force.

In another embodiment the diagnostic system includes computer readable instructions further comprising instructions for identifying an E-wave in the imaging data, instructions for determining from the E-wave a value of a spring constant k of a spring representative of chamber recoil, instructions for determining from the E-wave a value of a chamber viscoelastic damping constant c, instructions for determining from the E-wave a value of an initial displacement of the spring $x_o$, and instructions for using the values of the spring constant k, the values of the damping constant c, and the values of the initial displacement of the spring $x_o$, (derived from multiple E-waves acquired from beats at different load states), to calculate the load independent index of diastolic function (LIIDF) and the non-invasive estimate of left ventricular operating pressure (vertical intercept B).

These and other features, aspects and advantages of the present invention will become better understood with reference to the following description, examples and appended claims.

BRIEF DESCRIPTION OF THE SEVERAL VIEWS OF THE DRAWINGS

FIG. 3 B) shows maximum driving force ($kx_o$, peak AV gradient) vs. peak resistive force ($cE_{peak}$) for all (n=16) tilt table subjects at different load states, where reported values represent 5-beat average for $kx_o$ and $cE_{peak}$ for each subject at each load state;

FIG. 5 B) Maximum driving force ($kx_o$) vs. peak resistive force ($cE_{peak}$) for the three random E-waves shown in (a) (note deterioration of $r^2$);

FIG. 5 C) shows increase in randomly generated E-wave sample size to n=10 indicates further, substantial deterioration ($r^2$=0.01) of the observed, highly linear, maximum driving force ($kx_o$, peak AV gradient) to peak resistive force ($cE_{peak}$) relationship;

FIG. 6 A) shows deviations relative from the mean LVEDP (heavier lines denote average values, lighter lines above and below denote one standard deviation relative to the mean LVEDP);

FIG. 6 B) shows a regression slope (M) comparison between groups, where the thick-line is the average value from the tilt-table study, and dotted lines are one standard-deviation relative to the mean value;

FIG. 6 C) shows Intercept (B) comparison between groups, where the thick-line is average value from the tilt-table study, and dotted lines are one standard deviation relative to the mean intercept value;

Figure 11:
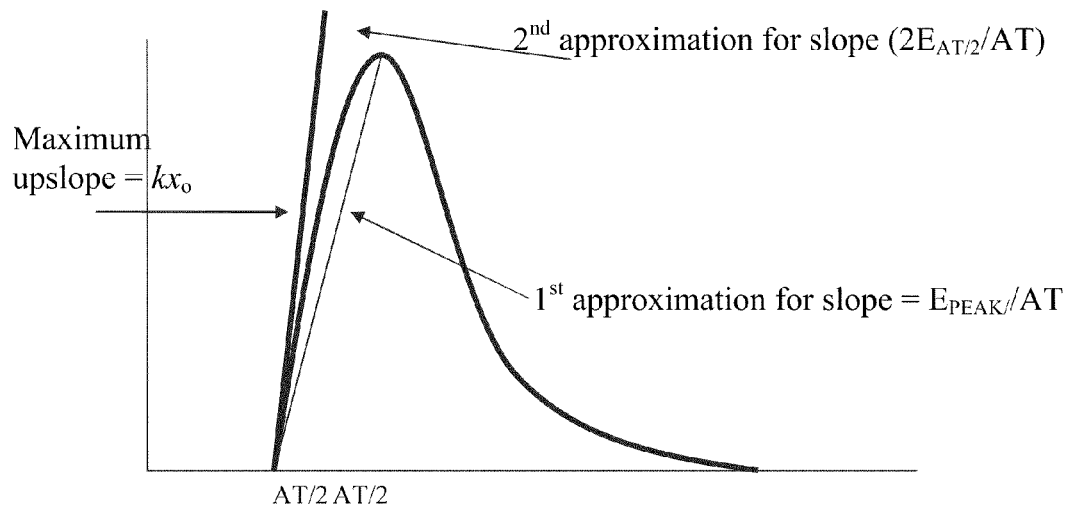
Figure 12:
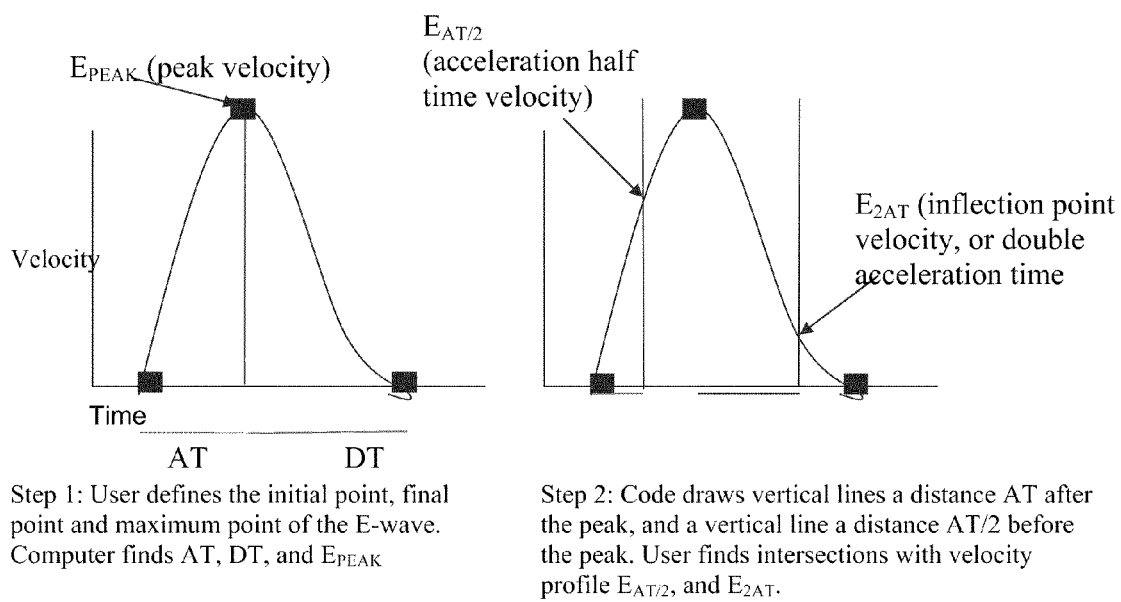
Figure 13:
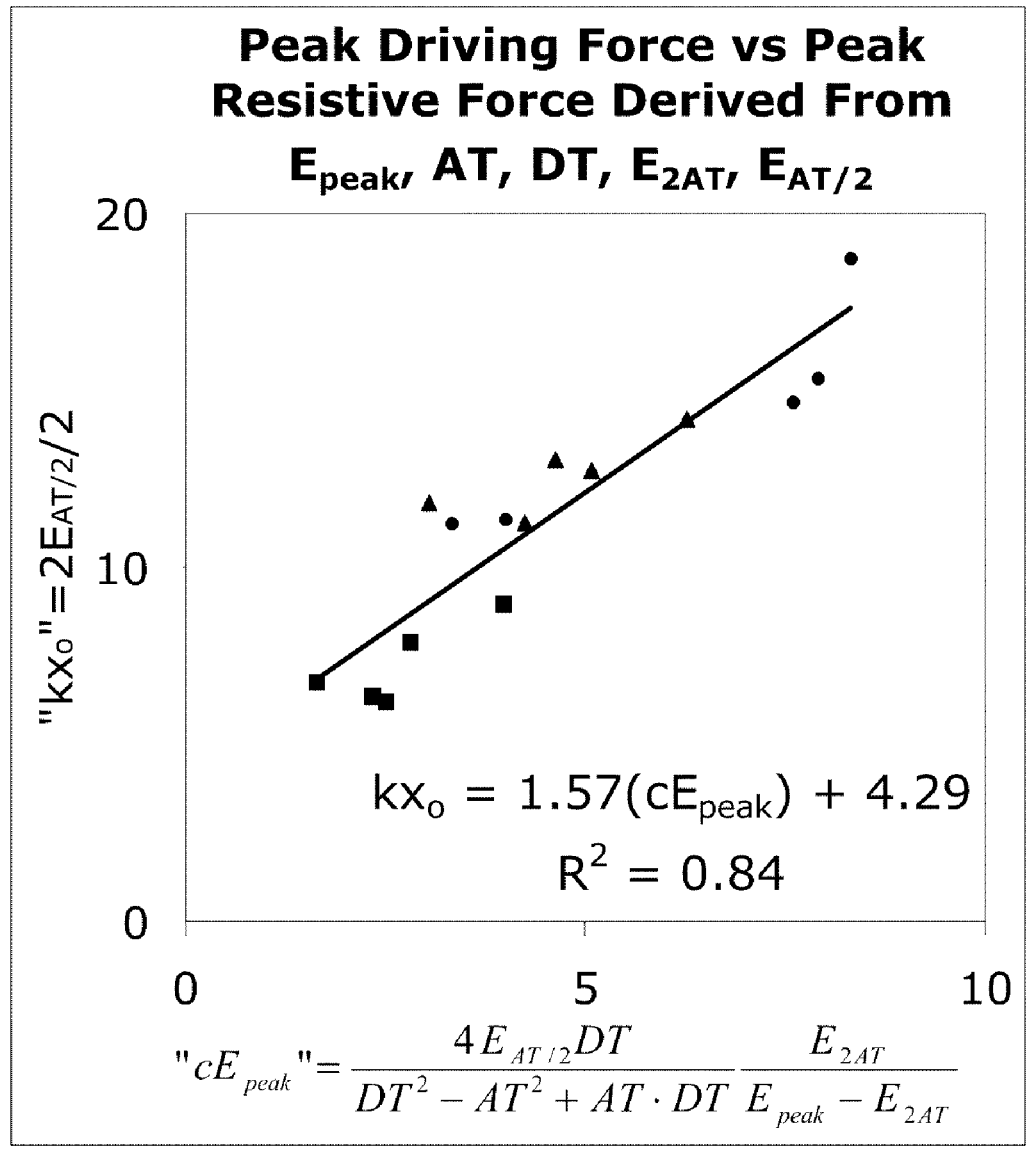
Figure 14:
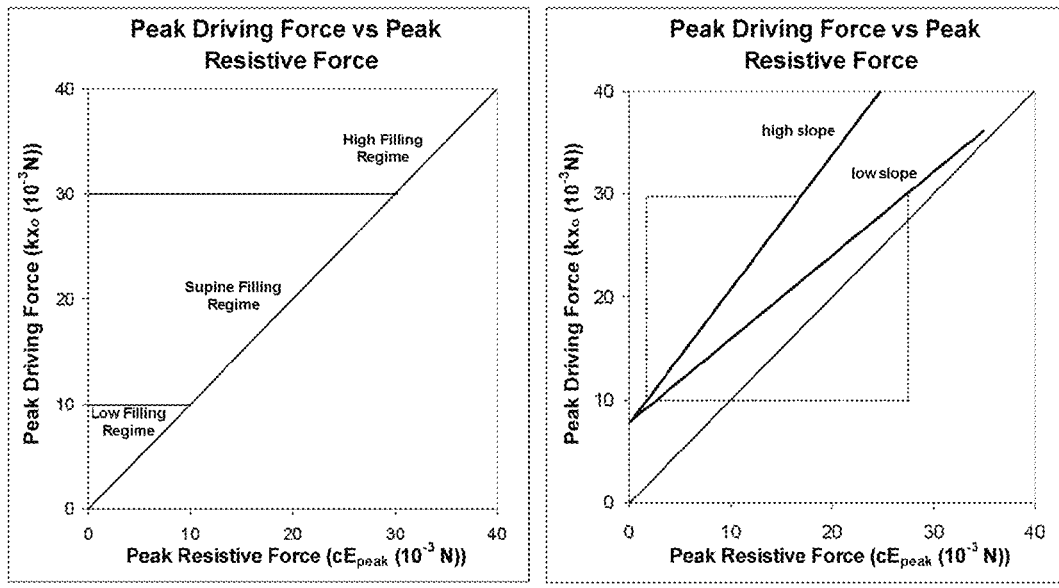
Figure 15:
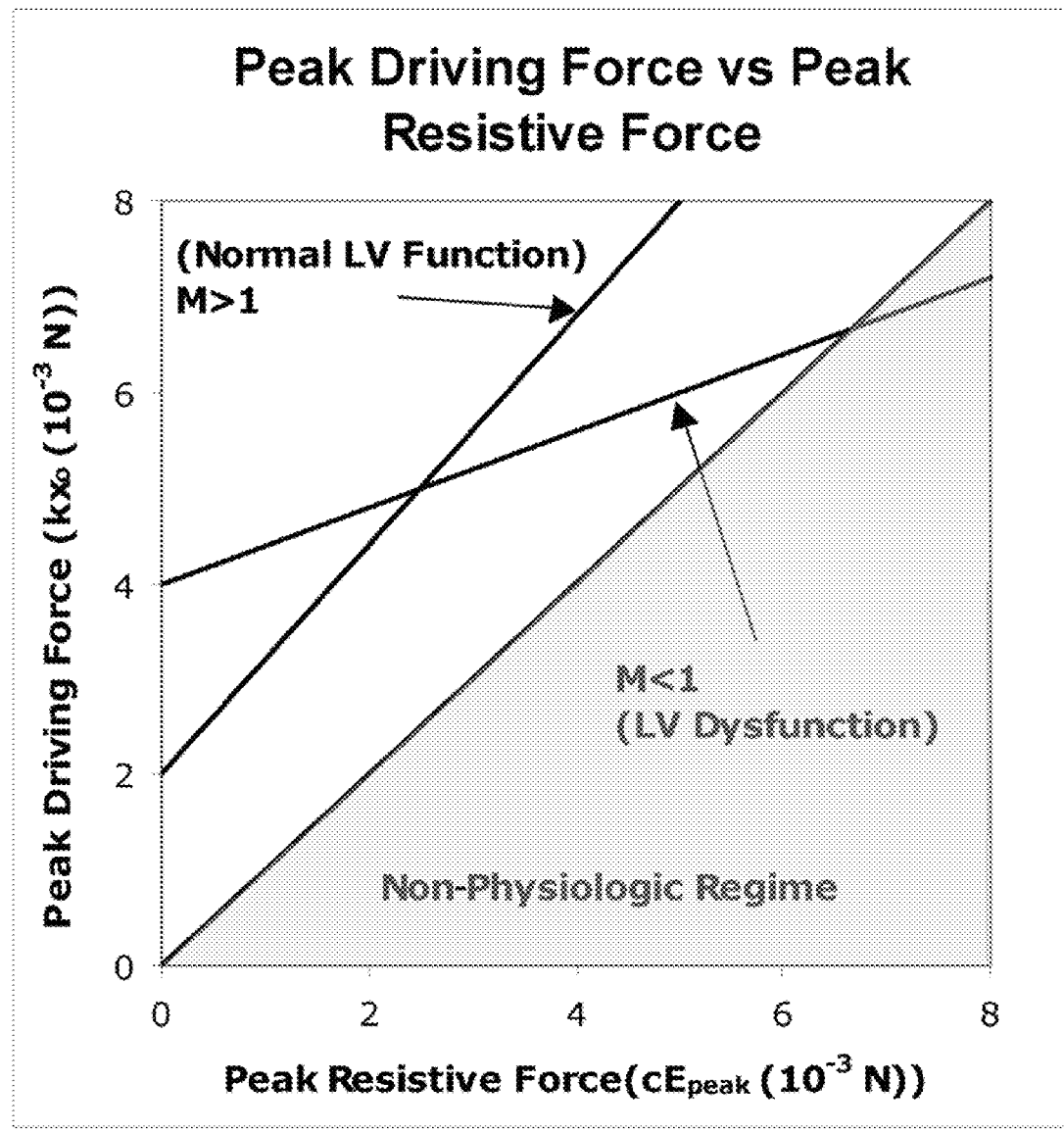
Figure 16:
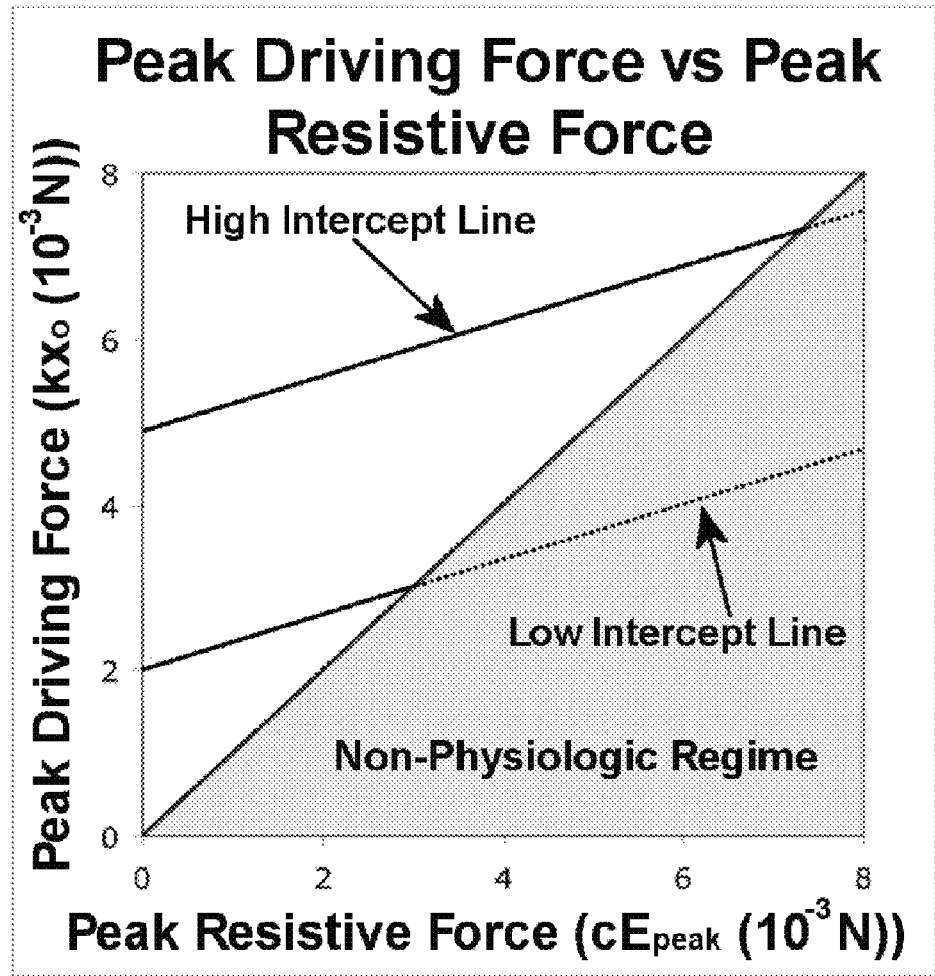
Figure 17:
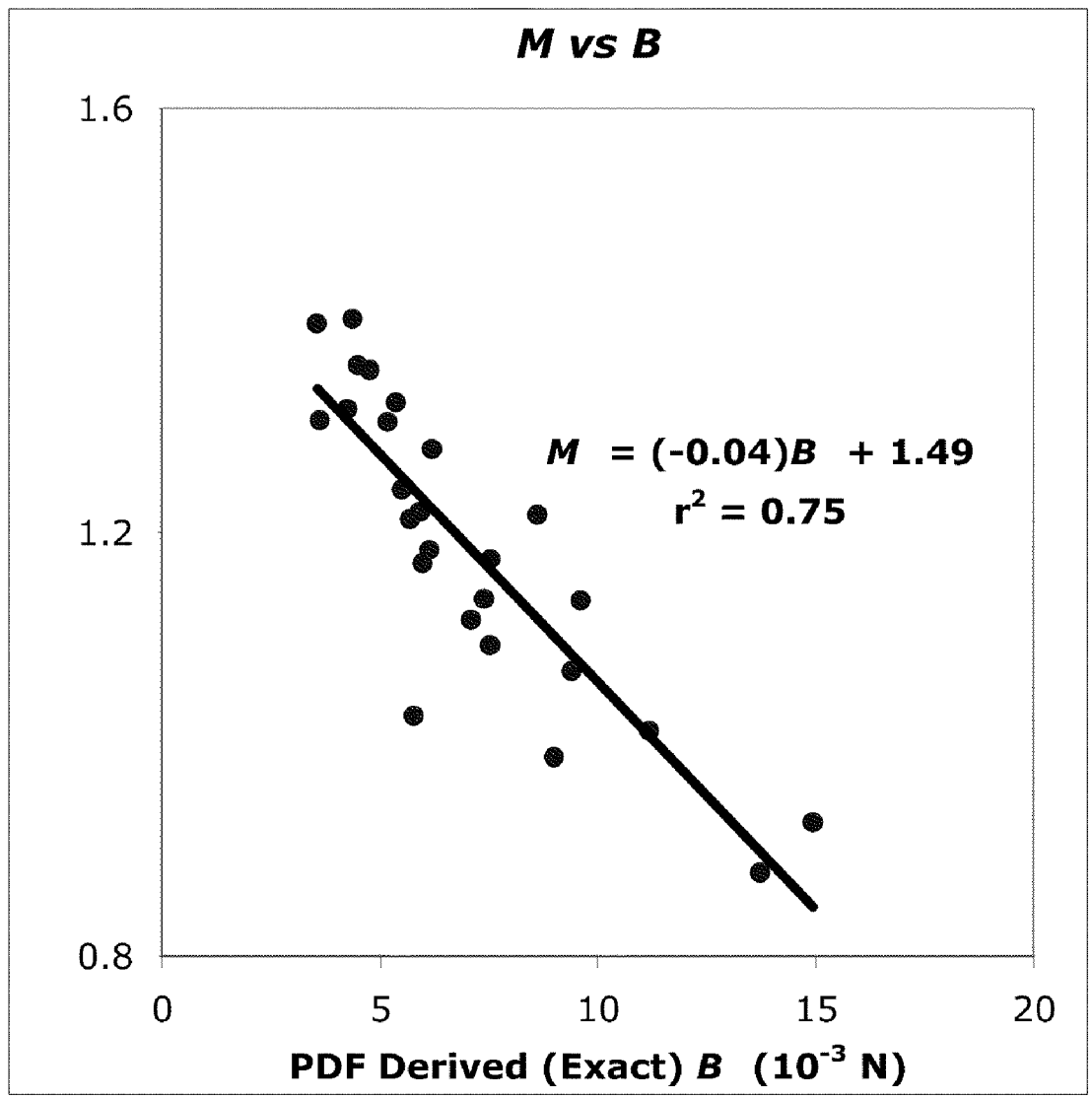

for one subject with load variation by tilt table maneuvers;

FIG. 11 shows the basis for the geometric refinements in the approximation of $kx_o$;

FIG. 12 demonstrates one embodiment of the method as implemented in a echocardiographic machine or offline analysis suite;

FIG. 13 is a graph of geometric maximum driving force ($2E_{AT/2}$/AT) versus geometric peak viscous/resistive force $$\left(\frac{4E_{AT \over 2} \cdot DT}{(DT^2 - AT^2 + AT \cdot DT)} \frac{E_{2AT}}{E_{peak} - E_{2AT}}\right)$$

for one subject with load variation by tilt table maneuvers;

FIG. 14 shows $kx_o$ vs $cE_{peak}$ graphs indicating different load regimes. The left panel shows low load, supine load, and high load regimes;

FIG. 15 is a graph of Peak Driving Force versus Peak Resistive Force illustrating physiological constraints governing filing;

FIG. 16 is a graph of Peak Driving Force versus Peak Resistive Force and two limits for a ventricle with low slope; and FIG. 17 shows the relationship between the LIIDF (M) and the noninvasive estimate of left ventricular operating pressure (B) for 26 subjects (15 heart healthy subjects undergoing tilt table variation, 6 cath-echo patients with diastolic dysfunction and 5 cath-echo control patients).

DETAILED DESCRIPTION OF THE INVENTION

The present invention is based in part on the discovery of a new method by which to analyze transmitral flow velocity waveforms and images, or tissue motion images, in order to compute a load-independent index of diastolic function. The methods and related systems are well-suited for analyzing imaging data such as that produced by imaging modalities such as Doppler echocardiograms, but can equally well be applied to analyzing waveforms and images obtained using other imaging modalities, both noninvasive and invasive. In particular, the present invention is based in part on the findings that the maximum driving force $kx_o$ and peak viscous/resistive force $cE_{peak}$ maintain a load independent and linear relationship as load is varied in the ventricle, and moreover that a determination of that relationship in a subject provides a load independent index of diastolic function (LIIDF) in the subject as well a non-invasive estimate of operating left ventricular pressures. Similarly, the inventors have discovered an equivalent approach that is non model-based (i.e does not require use of the PDF formalism) using values for the acceleration time of the E-wave (AT) from the E-waves whose shapes are approximated as triangles or as mathematically smoothed E-wave contours obtained by standard smoothing algorithms, values for the deceleration time of the E-wave (DT) from the same E-waves whose shapes are similarly approximated, and values for the peak amplitude of the E-wave ($E_{peak}$) from the E-waves whose shapes are similarly approximated, can be used to derive an analogous and related function describing the relationship of $E_{peak}/AT$ to $$\frac{E_{peak}}{AT} \frac{DT^2 - AT^2}{(DT^2 - AT^2 + AT \cdot DT)},$$

which, when plotted using values obtained at different loads also provides the LIIDF. Furthermore, the inventors have discovered an equivalent approach that is non model-based (i.e. does not require use of the PDF formalism) using values for the acceleration time of the E-wave (AT) from the E-waves whose shapes are approximated as triangles or as mathematically smoothed E-wave contours obtained by standard smoothing algorithms, values for the deceleration time of the E-wave (DT) from the same E-waves whose shapes are similarly approximated, and values for the peak amplitude of the E-wave ($E_{peak}$) from the E-waves whose shapes are similarly approximated, values for the amplitude of each E-wave at a time t=AT/2 ($E_{AT/2}$) from the exact E-wave shapes, and values for the amplitudes of each E-wave at a time t=2AT ($E_{2AT}$) from the exact E-wave shapes, can be used to derive an analogous and related function describing the relationship of $2E_{AT/2}/AT$ to $$\frac{4E_{\frac{AT}{2}} \cdot DT}{(DT^2 - AT^2 + AT \cdot DT)} \frac{E_{2AT}}{E_{peak} - E_{2AT}},$$

which, when plotted using values obtained at different loads also provides the LIIDF and non-invasive estimate of left ventricular operating pressures. The LIIDF and non-invasive estimate of left ventricular operating pressures can be obtained using data obtained from a variety of imaging modalities, including noninvasive and invasive modalities. Because the LIIDF is load independent, i.e. is not affected by load variation, the LIIDF is useful as direct indicator of instrinsic filling ability. The LIIDF can discriminate intrinsic changes in the condition of heart muscle or pumping chamber, versus changes in load conditions that are known to affect other, indirect measures of DF. The LIIDF can be used to evaluate intrinsic filling ability in various disease conditions, and also to evaluate therapeutic efficacy. It therefore can be used as a load independent measure of response to therapy, disease progression, regression, (termed beneficial remodeling) etc., to the extent that the disease affects the filling function of the heart.

On the other hand, the non-invasive estimate of left ventricular operating pressures can be used to monitor changes in left ventricular pressures often seen in heart disease, such as increased LVEDP, which is one hallmark of diastolic dysfunction. Using patients as their own controls, clinicians will be able to follow the progression of LVEDP over time and evaluate response to therapy.

Thus the LIIDF provides a previously unavailable and important tool for DF assessment, while the non-invasive estimate of left ventricular operating pressure provides an important tool for monitoring changes in left ventricular filling pressures.

Accordingly, in one embodiment there is provided a method for obtaining an index of cardiac function comprising obtaining imaging data representative of diastolic transmitral flow velocity or tissue motion at various (at least 2) load states in a subject, and analyzing the imaging data to determine a load-independent index of diastolic function in the subject. The imaging data must be acquired from several (at least 2) different load states. Analyzing the imaging data from each load state comprises, for example, identifying an E-wave in the imaging data, determining a value of peak-resistive force ($cE_{peak}$) from the E-wave, and determining a value of peak-driving force ($kx_o$) from the E-wave. Then a linear functional relationship between the values of the maximum driving force, determined at all load states, and the values of the peak resistive force, determined at all load states, is determined, and the slope and vertical intercept of the functional relationship between maximum driving force and peak resistive force is determined.

More specifically, a model-based image processing (MBIP) method as previously described is used in part to capture clinical E-wave and A-wave data, or imaging data representative of tissue motion. (A. F. Hall and S. J. Kovács Jr., "Automated method for characterization of diastolic transmitral Doppler velocity contours: Early rapid filling", Ultrasound in Medicine & Biology 20: 107-116 (1994); A. F. Hall et al., "Automated method for characterization of diastolic transmitral Doppler velocity contours: Late atrial filling", Ultrasound in Medicine & Biology 20: 859-869 (1994); A. F. Hall and S. J. Kovács Jr., "Model-Based Image Processing Of Doppler Velocity Profiles: Toward Automation", IEEE Ultrasonics, Ferroelectrics and Frequency Control Conference Proceedings, Seattle Wash. (1995)). Briefly, for example, clinical data of E- and A-waves for individual beats from a subject are analyzed by taking still images from the diastolic transmitral velocity profiles and calculating conventional Doppler-based diastolic function parameters such as $E_{peak}$, $E_{dur}$, AT, DT, $A_{peak}$, VTI and E/A ratio. E- and A-wave contours are fit by the solution to the equation of motion of a damped harmonic oscillator as described by the parameterized diastolic filling (PDF) formalism. (S. J. Kovács Jr. et al., "Evaluation of Diastolic Function with Doppler Echocardiography: The PDF Formalism", American Journal of Physiology 252:H178-H187 (1987)). The PDF formalism accounts for elastic, damping, and inertial forces that combine to generate mechanical, suction initiated transmitral flow. The contour of the E-wave is expressed as a closed-form mathematical expression. Known goodness of fit measures are then used to minimize the error between the model predicted fit and the clinical E-wave contour, which provides unique model parameters (c, k, $x_o$) for each E-wave. More specifically, the PDF formalism is used to determine: 1) a value of a spring constant k of a spring representative of chamber recoil, 2) a value of a chamber viscoelastic damping constant c, and 3) a value of an initial displacement of the spring $x_o$. The values of the spring constant k, the damping constant c, and the initial displacement of the spring $x_o$ are then used to generate values for maximum driving force ($kx_o$) and peak-resistive force ($cE_{peak}$) for the subject. The PDF formalism thus determines maximum driving force ($kx_o$) and peak resistive force ($cE_{peak}$) for one E-wave. One wave thus determines one point in the relationship between $kx_o$ and $cE_{peak}$. To generate a linear relationship between $kx_o$ and $cE_{peak}$ the variation of $kx_o$ and $cE_{peak}$ must be measured, specifically the variation of $kx_o$ and $cE_{peak}$ with changes in load. Load can be varied by multiple physiologic or pharmacologic methods, including but not limited to, tilt table (tilt-up decreases load, tilt-down increases load), leg lift while patient is supine (increases load), have patient sit up, then lie down, Valsalva maneuver (increases load), Mueller maneuver, and normal respiratory variation (load increases and decreases with expiration and inspiration respectively). The PDF formalism is used to analyze E-waves acquired at different loads, thus determining how $cE_{peak}$ and $kx_o$ change with load. The obtained load varying values for maximum driving force ($kx_o$) and peak-resistive force ($cE_{peak}$) for the subject are used to generate a function that describes the relationship between the two variables, namely a graph of maximum driving force $kx_o$ vs. peak resistive force $cE_{peak}$. The constant slope (M) of the straight-line graph relating maximum driving force $kx_o$ vs. peak resistive force $cE_{peak}$ is the load-independent index of diastolic function (LIIDF), while the intercept (B) of the straight-line graph relating maximum driving force $kx_o$ vs. peak resistive force $cE_{peak}$ is the non-invasive estimate of left ventricular operating pressure.

The method for obtaining the LIIDF and the non-invasive estimate of left ventricular operating pressure can be applied to imaging data obtained using non-invasive imaging modalities, such as Doppler echocardiography, cardiac MRI, CT scans or nuclear medicine scans of LV volume variation throughout the cardiac cycle, or using an invasive imaging modality such as cardiac catheterization/ventriculography, or LV volume determination via a conductance catheter. In one embodiment, for example, the spring constant k, the damping constant c, and the initial displacement of the spring $x_o$ are determined from an E-wave identified in imaging data representative of diastolic transmitral blood flow velocity. Imaging data representative of tissue motion can also be used.

Figure 10:
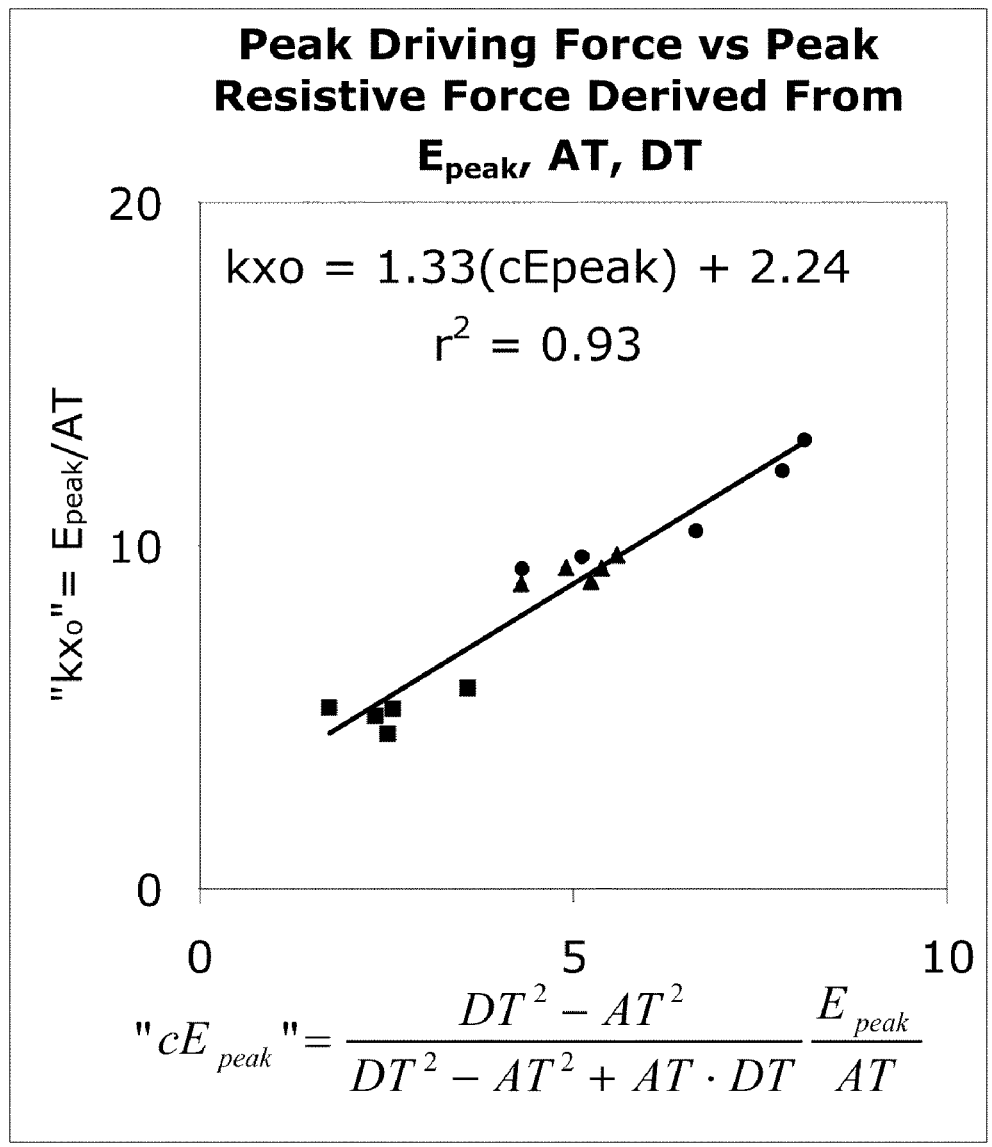
FIG. 10 is a graph of geometric maximum driving force ($E_{peak}$/AT) versus geometric peak viscous/resistive force $$\left(\frac{E_{peak}}{AT} \frac{DT^2 - AT^2}{(DT^2 - AT^2 + AT \cdot DT)}\right)$$

Alternatively, a model independent method is used to derive the LIIDF and the non-invasive estimate of left ventricular operating pressure, which corresponds to, and independently validates, the PDF model-based derivation of the LIIDF. This alternative PDF model independent method, begins with conventional E-wave shape based parameters derived from analysis of the load varying E-waves whose shape is approximated as a triangle or a suitably mathematically smoothed equivalent contour, namely the peak amplitude of each E-wave ($E_{peak}$), and the acceleration and deceleration times of each E-wave (AT and DT). The resulting data (acquired from subjects in several (at least 2) load states), is graphed as geometric maximum driving force $E_{peak}$/AT vs. geometric peak resistive force $$\frac{E_{peak}}{AT} \frac{DT^2 - AT^2}{(DT^2 - AT^2 + AT \cdot DT)},$$

generating a linear function with slope (M) and intercept (B) such as that shown in FIG. 10. The constant slope of the function is an E-wave shape-derived LIIDF which also happens to validate the true load independence of the LIIDF derived from the model based method described supra and in more detail in the Examples infra.

FIG. 10 is a graph of geometric maximum driving force ($E_{peak}$/AT) versus geometric peak viscous/resistive force $$\left( \frac{E_{peak}}{AT} \frac{DT^2 - AT^2}{(DT^2 - AT^2 + AT \cdot DT)} \right)$$

for one subject with load variation by tilt table maneuvers. Points of head up tilt are represented by squares, supine tilt by triangles, and head down tilt by circles. E-wave at varying loads were acquired and fit by simple well established triangular geometric approximations. Thus the LIIDF was derived purely from geometric parameters ($E_{peak}$, AT, DT) obtained from the geometric shape of the E-wave.

Furthermore, an additional and more refined model-independent method is used to derive the LIIDF and the non-invasive estimate of left ventricular operating pressure, which corresponds to, and independently validates, the PDF model-based derivation of the LIIDF. This alternative and more refined PDF model-independent method, begins with conventional E-wave shape based parameters derived from analysis of the load varying E-waves whose shape is approximated as a triangle or a suitably mathematically smoothed equivalent contour, namely the peak amplitude of each E-wave ($E_{peak}$), and the acceleration and deceleration times of each E-wave (AT and DT). Additionally, the amplitude of each E-wave is determined at a time of t=2AT ($E_{2AT}$) and at a time of t=AT/2 ($E_{AT/2}$). The resulting data (acquired from subjects in several (at least 2) load states), is graphed as geometric maximum driving force ($2E_{AT/2}$/AT or more refined estimate to the initial maximum upslope of each E-wave contour) vs. geometric peak resistive force $$\frac{4E_{\frac{AT}{2}} \cdot DT}{(DT^2 - AT^2 + AT \cdot DT)} \frac{E_{2AT}}{E_{peak} - E_{2AT}},$$

generating a linear function with slope (M) and intercept (B) such as that shown in FIG. 13. The constant slope of the function is an E-wave shape-derived LIIDF which also happens to validate the true load independence of the LIIDF derived from the model based method described supra and in more detail in the Examples infra. The unique vertical intercept B is an E-wave shape-derived noninvasive estimate of left ventricular operating pressure described supra and in more detail in the Examples infra.

FIG. 13 is a graph of geometric maximum driving force ($2E_{AT/2}$/AT) versus geometric peak viscous/resistive force $$\left( \frac{4E_{\frac{AT}{2}} \cdot DT}{(DT^2 - AT^2 + AT \cdot DT)} \frac{E_{2AT}}{E_{peak} - E_{2AT}} \right)$$

for one subject with load variation by tilt table maneuvers. Points of head up tilt are represented by squares, supine tilt by triangles, and head down tilt by circles. E-wave at varying loads were acquired and fit by simple well established triangular geometric approximations. Thus the LIIDF and non-invasive estimate of left ventricular operating pressures was derived purely from geometric parameters ($E_{peak}$, $E_{AT/2}$, $E_{2AT}$, AT, DT) obtained from the geometric shape of the E-wave.

All approaches for obtaining the LIIDF and the non-invasive estimate of left ventricular operating pressure can be made fully automated and can be embodied in computer readable media such as software or firmware for computerized applications. The methods are well-suited for applications in stand alone medical devices or in devices which are configured to connect with existing imaging devices or equipment such as imaging equipment. For example, computer readable media embodying computer readable instructions for computing the LIIDF and the non-invasive estimate of left ventricular operating pressure from imaging data can be incorporated in any commercially available echocardiography device. It is contemplated that an automated system based on the LIIDF methods described herein can be configured in various ways to require more or less interaction of a human operator or technician for capturing the required information from an initial input of imaging data. However, it should be clear that systems are contemplated which demand no more human interaction or expertise than is currently required of, for example, a typical echocardiography technician, i.e. a sonographer. Accordingly, in another embodiment, the invention embraces a system for analyzing cardiac function in a subject, which is suitable for computer applications which can provide automated determination of the LIIDF and the non-invasive estimate of left ventricular operating pressure in a subject. The system includes, for example, a computer usable medium which embodies computer readable code including instructions to a computer for receiving an input of imaging data representative of diastolic transmitral flow velocity or of tissue motion, or of measurements of the triangle shape approximation to the E-wave such as AT, DT or $E_{peak}$ in a subject, or of measurements of the triangle shape approximation to the E-wave such as AT, DT, and $E_{peak}$ coupled with measurements of the E-wave amplitude at t=AT/2 and t/2AT ($E_{AT/2}$, $E_{2AT}$ respectively). Again, the imaging data can be obtained from modalities including but not limited to, for example, a Doppler echocardiography, cardiac MRI, CT scanning, nuclear cardiology imaging methods or cardiac catheterization. The computer readable code further includes instructions to the computer to generate the LIIDF and the non-invasive estimate of left ventricular operating pressure in the subject from the imaging data, according to methods described herein. The LIIDF and the non-invasive estimate of left ventricular operating pressure can be derived using the PDF model based approach, or the non-PDF model based approach using $E_{peak}$, DT, and AT, or the non-PDF model based approach using $E_{peak}$, DT, AT, $E_{2AT}$, $E_{AT/2}$, or a combination of any of the methods.

The system can, for example, include the computer itself, which is configured to operate at least in part according to the instructions embodied on the computer usable medium. In one embodiment, the system includes also display apparatus such as, for example, a visual display screen, which is operatively coupled to the computer. The display apparatus displays, for example, visual images representative of the imaging data and graphic representations of the LIIDF and the non-invasive estimate of left ventricular operating pressure optionally including graphic representations of the supporting calculations and linear functions.

In another embodiment, the system includes computer readable code comprising instructions to a computer to perform the following steps: identify an E-wave in the imaging data, determine a value of peak resistive force ($cE_{peak}$) from the E-wave, and determine a value of peak-driving force ($kx_o$) from the E-wave. These mentioned steps must be repeated for several E-waves acquired at different load states (at least 2 different load states. Once several E-waves acquired from different load states are analyzed by the above steps the computer must perform the following steps: generate a linear function describing a relationship of the maximum driving force versus peak resistive force, and determine a slope and vertical intercept of the function of maximum driving force versus peak resistive force.

In another embodiment, the system includes computer readable code comprising instructions to a computer to perform the following steps: identify an E-wave in the imaging data, determine a value for peak amplitude of the E-wave ($E_{peak}$) from the E-wave, determine a value for a deceleration time and acceleration time (DT, AT) of the E-wave by approximating its shape as a triangle or other smoothed contour using image processing methods, and determine the geometric maximum driving force and geometric peak resistive force by calculation (geometric maximum driving force=$E_{peak}$/AT, $$\text{geometric peak resistive force} = \frac{E_{peak}}{AT} \frac{DT^2 - AT^2}{(DT^2 - AT^2 + AT \cdot DT)}\right).$$

These mentioned steps must be repeated for several E-waves acquired at different load states (at least 2 different load states. Once several E-waves acquired from different load states are analyzed by the above steps the computer must perform the following steps: generate a linear function describing a relationship of the geometric maximum driving force ($E_{peak}$/AT) to the geometric peak resistive force $$\left(\frac{E_{peak}}{AT} \frac{DT^2 - AT^2}{(DT^2 - AT^2 + AT \cdot DT)}\right),$$

and determine a slope and vertical intercept of the function of geometric maximum driving force versus geometric peak resistive force.

In another embodiment, the system includes computer readable code comprising instructions to a computer to perform the following steps: identify an E-wave in the imaging data, determine a value for peak amplitude of the E-wave ($E_{peak}$) from the E-wave, determine a value for a deceleration time and acceleration time (DT, AT) of the E-wave by approximating its shape as a triangle or other smoothed contour using image processing methods, determine a value for the amplitude of the E-wave at a time t=AT/2 ($E_{AT/2}$), determine a value for the amplitude of the E-wave at a time t=2AT ($E_{2AT}$), and determine the geometric maximum driving force and geometric peak resistive force by calculation (geometric maximum driving force=$2E_{AT/2}$/AT or equivalent estimate for the maximum initial upslope of the E-wave, $$\text{geometric peak resisitive force} = \frac{4E_{AT} \cdot DT}{(DT^2 - AT^2 + AT \cdot DT)} \frac{E_{2AT}}{E_{peak} - E_{2AT}}\right).$$

These mentioned steps must be repeated for several E-waves acquired at different load states (at least 2 different load states. Once several E-waves acquired from different load states are analyzed by the above steps the computer must perform the following steps: generate a linear function describing a relationship of the geometric maximum driving force ($2E_{AT/2}$/AT or equivalent estimate for the maximal initial upslope of the E-wave) to the geometric peak resistive force $$\left( \frac{4E_{\frac{AT}{2}} \cdot DT}{(DT^2 - AT^2 + AT \cdot DT)} \frac{E_{2AT}}{E_{peak} - E_{2AT}} \right),$$

and determine a slope (M) and vertical intercept (B) of the function of geometric maximum driving force versus geometric peak resistive force.

In another embodiment, the system includes computer readable code comprising instructions to a computer to perform the following steps: identify an E-wave in the imaging data; determine from the E-wave a value of a spring constant k of a spring representative of chamber recoil, determine from the E-wave a value of a chamber viscoelastic damping constant c; determine from the E-wave a value of an initial displacement of the spring $x_o$; repeat these steps for several E-waves acquired from the subject at different load states, use the values of the spring constant k, the values of the damping constant c, and the values of the initial displacement of the spring $x_o$ to calculate a load independent index of diastolic function and a non-invasive estimate of left ventricular operating pressure, according to the methods described herein.

In another embodiment the invention encompasses apparatus for displaying indices of cardiac function in a subject. Such apparatus is contemplated as being useful, for example, as an instructional tool for medical personnel or monitoring device for medical personnel monitoring patients. Such apparatus includes, for example, a computer usable medium comprising computer readable code embodied therein which includes instructions for receiving an input of imaging data representative of diastolic transmitral flow velocity or tissue motion in a subject or the rate of change of ventricular volume from any other imaging modality. The computer readable code further includes instructions for generating an LIIDF and a noninvasive estimate of left ventricular operating pressure in the subject from the imaging data. Visual display apparatus such as, for example, a video monitor or other computer monitor is operatively coupled to the computer usable medium, and the visual display apparatus receiving instructions from the computer usable medium is configured to display the imaging data and a visual representation of the LIIDF and noninvasive estimate of left ventricular operating pressure such as a numerical figure, graphical representations of the LIIDF and noninvasive estimate of left ventricular operating pressure or of related calculations as described herein.

In yet another embodiment the invention contemplates a diagnostic system for analyzing cardiac function in a subject, or for automated screening of multiple subjects. The system includes, for example, a computer processor. The computer processor is configured with computer readable instructions, for example embodied on a computer usable medium. The instructions include instructions for the steps of receiving and storing an input of imaging data representative of diastolic transmitral flow velocity at different load states, or of tissue motion in a subject. The instructions also include instructions to the computer processor for generating an LIIDF and noninvasive estimate of left ventricular operating pressure in the subject from the imaging data obtained at different load states. The instructions for generating the LIIDF and noninvasive estimate of left ventricular operating pressure can include instructions according to the model-based method for determining LIIDF and noninvasive estimate of left ventricular operating pressure, or instructions according to the non-model, shape-based methods for determining LIIDF and noninvasive estimate of left ventricular operating pressure, or for both.

Other Embodiments

The invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. For example, the methods and related systems are especially well-suited for Doppler echocardiogram images, but can equally well be applied to analyzing waveforms and images obtained using other imaging modalities, both noninvasive and invasive, including but not limited to cardiac magnetic resonance imaging (MRI), radionuclear imaging, CT scans and cardiac catheterization and nanomedicine/nanotechnology based imaging modalities. Any imaging modality that provides data indicative of ventricular volume as a function of time, i.e. the volumes of the ventricles and rates of change of the volumes, can be used to provide data suitable for analysis according to the methods and apparatus of the present invention. In addition, numerous refinements can be made to the non-model based geometric approximation methods for determination of the LIIDF and the noninvasive estimate of left ventricular operating pressures. Geometric based estimates of the maximum driving force $kx_o$ that more closely approximate the maximum initial upslope of the E-wave will more closely approximate the maximum driving force $kx_o$ and lead to better geometric predictions of $cE_{peak}$ $$\left( \text{initial } upslope_{max} \cdot \frac{DT^2 - AT^2}{DT^2 - AT^2 + AT \cdot DT} \right).$$

Accordingly, the following experimental examples describing a load independent index of diastolic function are offered by way of illustration and not by way of limitation.

A kinematic modeling approach, motivated by the role of all ventricles as mechanical suction pumps (dP/dV<0) in early diastole, equates early rapid filling velocity with the velocity of a previously stretched, recoiling damped linear oscillator. This approach is motivated by the premise that the motion of the heart is governed by Newton's Law of Motion and must be the result of the balance between elastic, inertial and viscous/resistive forces. Several studies have shown that Titin (H. L. Granzier and S. Labeit, "The giant protein titin: a major player in myocardial mechanics, signaling, and disease", Circ Res. 94(3): 284-295 (2004) and the extra cellular connective tissue matrix (T. F. Robinson et al., "The heart as a suction pump", Sci Am 254: 84-91 (1986)) provide elastic spring (restoring) force to lengthen myocytes and enlarge the chamber during early-rapid ventricular filling (E-wave). These restoring forces are opposed by the inertia of the moving tissue and blood as well as the (lumped) viscous/resistive losses in the system. The parameterized diastolic filling (PDF) formalism combines all of these effects and accounts for elastic, damping, and inertial effects via Newton's Law (1).

$$m\frac{d^2x}{dt^2} + c\frac{dx}{dt} + kx = 0 \qquad [1]$$

Solution of Equation [1] for the velocity (dx/dt) expresses the transmitral flow velocity (E-wave contour) as a closed-form mathematical expression. The model parameters c, k, $x_o$ correspond to an equivalent damping constant, spring constant, and initial spring displacement respectively. The velocity of the spring as a function of time is therefore equivalent to the velocity profile of the blood flowing across the mitral valve during diastole. The parameters are determined from the clinical E-wave contour via model-based image processing (MBIP) which generates unique numerical values of the parameters by minimizing measures of goodness of fit between the Doppler determined E-wave contour and the model predicted solution to the equation of motion for the simple harmonic oscillator (SHO) (Newton's Law) (FIG. 1).

Figure 1:
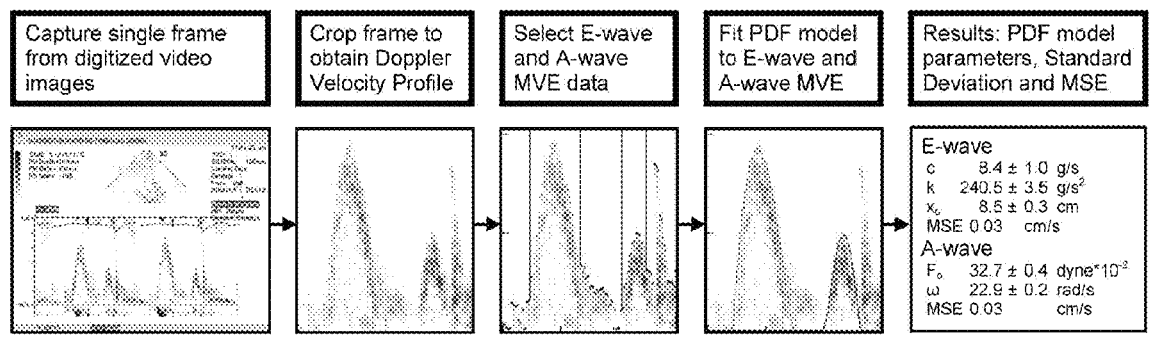
FIG. 1 describes the Model Based Image Processing (MBIP) method by which PDF parameters are computed.

FIG. 1 describes the Model Based Image Processing (MBIP) method by which PDF parameters are computed. A video frame with the Doppler image is captured, and digitized, and an isolated diastolic interval is cropped. Then a maximum velocity envelope (MVE) of the E and A-waves is defined, and a mathematical algorithm is used to fit the wave by iteratively changing values for k, c, and $x_o$.

One beneficial consequence of the PDF model is the ability to use the kinematics of the oscillator to relate the PDF parameters to the physiology of diastole. Specifically: the chamber stiffness (dP/dV) is linearly related to k (J. B. Lisauskas et al. "Chamber properties from transmitral flow: prediction of average and passive left ventricular diastolic stiffness." *J Appl Physiol.* 91: 154-162 (2001)); the initial force $kx_o$ is the analog of the peak atrioventricular pressure gradient generating transmitral blood flow (L Bauman et al. "The peak atrioventricular pressure gradient to transmitral flow relation: kinematic model prediction with in-vivo validation." *J Am Soc Echocardiogr* 8:839-844, (2004)); $\frac{1}{2}k(x_o)^2$ is the energy (ergs) available prior to valve opening (S. J. Kovács Jr., et al., "Modelling cardiac fluid dynamics and diastolic function", *Philosophical Transactions of the Royal Society (A)*:359, 1299-1314 (2001)) and $x_o$ is the VTI of the E-wave (S. J. Kovács Jr., et al., "Modeling of Diastole" *Cardiology Clinics of North America*, 18(3): 459-490 (2000)). Table 1 summarizes PDF parameter physiologic analogues.

TABLE 1

Physiologic Analogues of PDF parameters and parameter-derived indexes

| PDF parameter or index | Physiologic Analogue | Significant Findings |
|---|---|---|
| k (g/s$^2$) | Chamber stiffness ($\Delta P/\Delta V$) | k is linearly related to chamber stiffness, $\Delta P/\Delta V$ (J. B. Lisauskas et al. "Chamber properties from transmitral flow: prediction of average and passive left ventricular diastolic stiffness." J Appl Physiol. 91: 154-162 (2001)) |
| c (g/s) | Viscoelastic index | In normal LVEF diabetic rats (C. L. Dent et al. "Echocardiographic characterization of fundamental mechanisms of abnormal diastolic filling in diabetic rats with a parameterized diastolic filling formalism." J Am Soc Echocardiogr, 14: 1166-1172 (2001)) and humans(M. M. Riordan et al. "Diabetes and Diastolic Dysfunction: Stiffness and relaxation from transmitral flow." Ultrasound in Med. & Biol., 31(12): 1589-1596 (2005)) c, but not k, is significantly higher, compared to non-diabetic controls |
| $x_o$ (cm) | Effective volumetric load | $x_o$ is linearly related to the velocity-time integral of the E wave (S. J. Kovács Jr., et al., "Modeling of Diastole" Cardiology Clinics of North America, 18(3): 459-490 (2000)) |
| $kx_o$ (gcm/s$^2$) | Peak A-V pressure gradient | $kx_o$ model-derived peak driving force, correlates with peak AV gradient better than $4v^2$ (L. Bauman et al. "The peak atrioventricular pressure gradient to transmitral flow relation: kinematic model prediction with in-vivo validation." J Am Soc Echocardiogr 8: 839-844, (2004)) |
| $cE_{peak}$ (gcm/s$^2$) | Maximum resistive force opposing filling | The slope of the $cE_{peak}$ and $kx_o$ (peak A-V gradient) relationship is a load independent index of diastolic filling (L. Shmuylovich and S. J. Kovács, "A load independent index of diastolic filling: model-based derivation with in-vivo validation in control and diastolic dysfunction subjects." J Appl Physiol. 2006; 101: 92-101.) |
| $\frac{1}{2}kx_o^2$ (J) | Stored elastic strain energy | Initial, (maximum) potential energy available to power filling (S. J. Kovács Jr., et al., "Modelling cardiac fluid dynamics and diastolic function", Philosophical Transactions of the Royal Society (A): 359, 1299-1314 (2001)) |

E-wave velocity contours are known to be load dependent, and because the PDF formalism provides an excellent fit to all observed E-waves, the PDF parameters will change as E-waves change in response to a change in load.

Derivation of a Load-Independent Index

To derive a load independent index, a goal was to decouple load ($x_o$) from filling by employing the kinematic model of filling (the PDF model). Specifically, noting that regardless of how E-wave contours respond to variations in load, the equation of motion (Newton's law), which includes inertial, damping and recoil forces for the SHO, remains valid. The equation that approximates the E-wave is:

$$m\frac{d^2x}{dt^2} + c\frac{dx}{dt} + kx = 0 \quad [2]$$

where m, c and k denote inertia, damping and spring constants respectively. This relationship applies at all times, including at $t=t_{peak}$ when the peak of the E wave is inscribed. The acceleration term $d^2x/dt^2$ is zero at $t=t_{peak}$. Changing notation so that dx/dt (velocity of the damped spring) is expressed as E-wave peak velocity, and Eq [2] becomes:

$$cE_{peak} + kx(t_{peak}) = 0 \quad [3]$$

Because the peak velocity is attained quickly, the instantaneous driving force exerted by the spring at peak velocity, $kx(t_{peak})$, can be linearly approximated by the initial, maximum driving force $kx_o$, the model's analogue of the peak AV (atrioventricular) gradient. This linear relationship can be approximated as:

$$kx(t_{peak})=M'(kx_o)+B' \quad [4]$$

and therefore approximate and rewrite [3] as $$(kx_o)=M(cE_{peak})+B \quad [5]$$

where $kx_o$ is the mathematical analogue for the maximum AV gradient and $cE_{peak}$ represents the resistive (viscoelastic) force opposing filling. Hence the relation (slope M) between maximum driving force and peak viscous force ($kx_o$ vs. $cE_{peak}$) should be linear and should be load independent. This predicted linearity between maximum driving force $kx_o$ and peak resistive force $cE_{peak}$ should be load independent because it is derived from equations and approximations that are load independent.

The following non-limiting examples are provided to further illustrate the present invention. It should be appreciated by those of skill in the art that the techniques disclosed in the examples that follow represent approaches that the inventors have found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Pulsed Doppler echocardiography in accordance with ASE (American Society of Echocardiography) criteria (CP Appleton, "Doppler evaluation of left and right ventricular diastolic function: a technical guide for obtaining optimal flow velocity recordings." *J Am Soc Echocardiogr* 10: 271-291, 1997) was used to acquire continuous transmitral blood flow data from 15 subjects (ages 20-30) while the subjects were positioned on a tilt-table at a variety of tilt angles. The subjects were normal healthy volunteers, on no prescribed medications, with no history of heart disease. Prior to participation in the study, all subjects gave informed consent in accordance with the Washington University Medical College Human Studies Committee guidelines.

Doppler data was obtained with a clinical echocardiographic imaging system (Acuson Sequia 256, Mountain View, Calif.) equipped with a 2 MHz transducer. Transmitral E- and A-waves were recorded using the 4-chamber view with the transducer positioned apically and the sample volume located at the mitral valve leaflet tips. Heart rate (HR) was recorded simultaneously via ECG limb lead II and displayed on the E- and A-wave images. Blood pressure was monitored via a digital blood pressure cuff.

The data acquisition protocol consisted of initial, baseline E- and A-wave recording with the subject supine and the tilt table in the horizontal position for 5 minutes such that the heart rate was in steady state. Baseline blood pressure measurements were obtained. After 5 minutes in the supine position, the table, including appropriate padding and straps to assure safety was gradually tilted to a 90° head-down position. Since the heart/diaphragm shifted during the tilt procedure the transducer was suitably reoriented to obtain transmitral flow. Once reoriented, and after the heart rate stabilized in this position, typically after several minutes, E- and A-waves were again recorded. After 5 minutes in the head down position the tilt-table was gradually returned back to the horizontal position where, after heart rate and BP transients had subsided, and returned to baseline levels, E- and A-waves were again recorded. Once completed, the tilt table was gradually tilted to a 90° head up position so that the subjects were in a standing position. The transducer location was adjusted slightly to account for the shifting of the heart during tilt, after heart rate and blood pressure transients resolved E- and A-waves were recorded during a 5 minute interval. After 5 minutes in the upright position the subjects were tilted back to the horizontal position where a final set of E- and A-waves were recorded.

All E- and A-wave data were recorded on VHS tape for subsequent off-line analysis using a custom video editing station. A model-based image processing (MBIP) method by which PDF parameters are obtained from frame grabbed (digitized) VHS recording of transmitral flow has been previously described. FIG. 1. (A. F. Hall and S. J. Kovács Jr., "Automated Quantification of Diastolic Filling Parameters from Cardiac Doppler Ultrasound", *Proceedings, 1992 IEEE Ultrasonics Symposium*, October: 1125-1128, Tucson, Ariz., (1992); Hall and S. J. Kovács Jr., "Processing parameter effects on the robustness of the solution to the "Inverse Problem" of diastole from Doppler echocardiographic data", *15th Annual International Conference, IEEE Engineering in Medicine & Biology Society*, 1385-387 (1993).

Briefly, E- and A-waves for individual beats were analyzed by taking still images from the transmitral velocity profiles and calculating conventional Doppler based diastolic function parameters such as $E_{peak}$, $E_{dur}$, AT, DT, $A_{peak}$ and E/A. In addition, E- and A-wave contours were fit by the solution to the equation of motion of a damped harmonic oscillator as described by the parameterized diastolic filling (PDF) formalism. The PDF formalism accounts for elastic, damping, and inertial forces that combine to generate mechanical, suction initiated transmitral flow. The contour of the E-wave is expressed as a closed-form mathematical expression.

Figure 2:
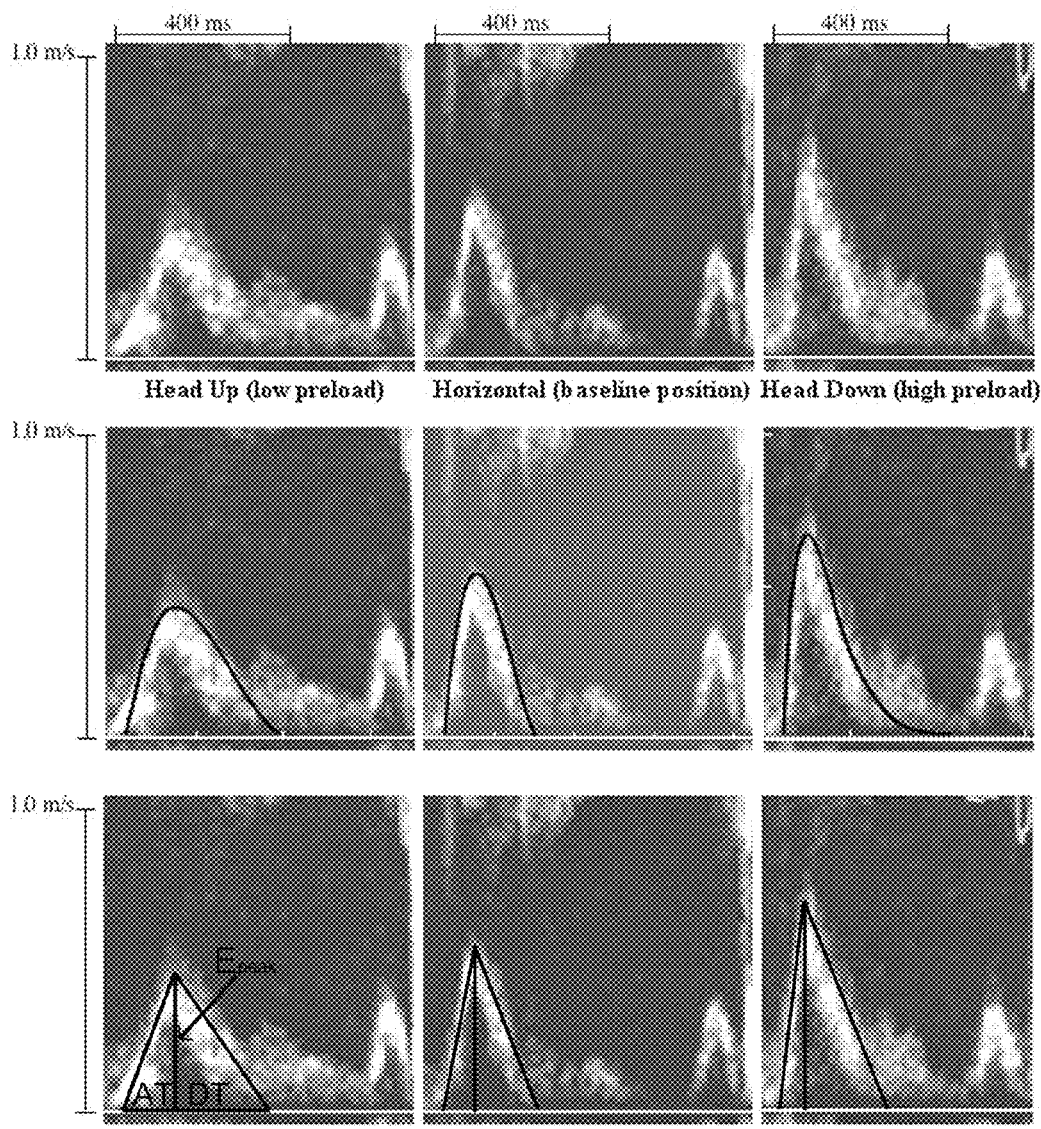
FIG. 2 shows pulsed wave transmitral flow-velocity images from one subject at three different load (tilt-table positions) states.

Minimizing the error between the model predicted fit and the clinical E-wave contour provides unique model parameters (c, k, $x_o$) for each E-wave. FIG. 2 shows representative E-waves from the same subject at different tilt-table positions, the shape based triangular fits, and the PDF determined fits to the E-wave.

FIG. 2 shows Pulsed wave transmitral flow-velocity images from one subject at three different load (tilt-table positions) states. Single diastolic interval at each tilt table position is shown. PDF model-predicted fit to each E wave is shown in middle panels. The bottom panels show typical geometric approximations to the three E-waves, characterizing the E-waves by 3 parameters (peak height $E_{peak}$, acceleration time AT, and deceleration time DT).

Example 2

Variation of E-Wave Shape with Tilt Table Position

In agreement with other studies (see, e.g. B. P. Paelinck et al. "Effects of postural changes on cardiac function in healthy subjects." *Er J Echocardiography* 4: 196-201 (2003)), both E- and A-wave shapes varied in response to changes in load generated by changes in tilt table position. Since the PDF parameters are determined from the contour of the waves, changes in load result in changes in the PDF parameters. Table 2 summarizes the average values for both traditional Doppler indexes and PDF parameters under different load states i.e. tilt-table positions.

Since subjects had a distribution of values for Doppler indexes and PDF parameter values in the horizontal tilt-table position, determining an average over all subjects required reference to a common baseline. Horizontal was chosen as the baseline tilt table position and all values were calculated as percent change from horizontal. Table 3 presents both PDF and traditional Doppler data as percent change from horizontal for both head-up and head-down tilt.

Example 3

Determination of Predicted Load Independence

In accordance with the prediction (equation [5]) that the maximum driving force must be linearly related to peak viscous (resistive) force, a linear regression via least mean square error of $cE_{peak}$ to $kx_o$ was performed. FIG. 3a shows a representative maximum driving force ($kx_o$) vs. peak resistive force ($cE_{peak}$) plot for one subject. Head-up data from two subjects was not included, but their head-down and horizontal data fit the maximum driving force ($kx_o$) vs. peak resistive force ($cE_{peak}$) regression with high $r^2$. Among all subjects, the average slope of the maximum driving force ($kx_o$) vs. peak resistive force ($cE_{peak}$) plot was 1.27±0.09 and the average intercept was 5.69±1.70. The average $r^2$ value for each subjects' linear regression was $r^2$=0.95. The combined data from all subjects plotted together yielded a linear regression with $r^2$=0.98 (FIG. 3b). The slope of the line, M, is a load-independent index of diastolic function.

Figure 3:
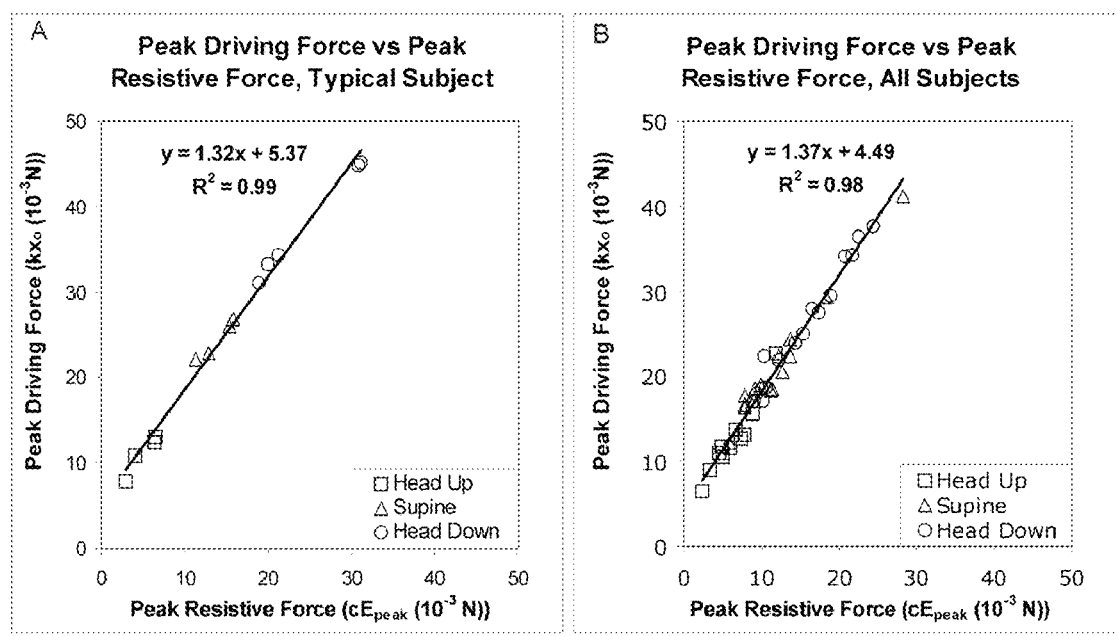
FIG. 3 A) shows maximum driving force ($kx_o$, peak AV gradient) vs. peak resistive force ($cE_{peak}$) for one subject at three different load states (slope of best linear fit is independent of tilt-table position)

FIG. 3 A) Maximum driving force ($kx_o$, peak AV gradient) vs. peak resistive force ($cE_{peak}$) for one subject at three different load states. Note slope of best linear fit is independent of tilt-table position.

FIG. 3 B) Maximum driving force ($kx_o$, peak AV gradient) vs. peak resistive force ($cE_{peak}$) for all (n=16) tilt table subjects at different load states. Reported values represent 5-beat average for $kx_o$ and $cE_{peak}$ for each subject at each load state.

TABLE 2

Average values of Doppler indices and PDF parameters in one typical tilt-table subject at three different load states

| | Head Up | Horizontal | Head Down |
|---|---|---|---|
| a) Average Doppler indices, one typical subject | | | |
| $E_{peak}$ (m/s) | 0.50 ± 0.05 | 0.55 ± 0.05 | 0.70 ± 0.04 |
| AT (s) | 0.11 ± 0.01 | 0.10 ± 0.01 | 0.09 ± 0.01 |
| DT (s) | 0.16 ± 0.03 | 0.14 ± 0.02 | 0.13 ± 0.01 |
| $E_{dur}$ (s) | 0.27 ± 0.03 | 0.24 ± 0.03 | 0.22 ± 0.02 |
| $A_{peak}$ (m/s) | 0.42 ± 0.04 | 0.36 ± 0.04 | 0.39 ± 0.04 |
| $A_{dur}$ (s) | 0.13 ± 0.01 | 0.13 ± 0.01 | 0.13 ± 0.01 |
| E/A | 1.2 ± 0.1 | 1.5 ± 0.1 | 1.8 ± 0.2 |
| HR (beats/min) | 58 ± 7 | 49 ± 2 | 56 ± 6 |
| b) Average PDF parameter values, same typical subject | | | |
| $c \cdot 10^3$ (1/s) | 5.6 ± 3.9 | 11.3 ± 3.0 | 16.2 ± 5.7 |
| $k \cdot 10^3$ (1/s$^2$) | 113 ± 24 | 198 ± 31 | 249 ± 21 |
| $x_o$ (m) | 0.06 ± 0.01 | 0.06 ± 0.00 | 0.08 ± 0.02 |

TABLE 3

Averaged, normalized percent increase (+) or decrease (−) relative to baseline (horizontal tilt-table position) for all (n = 16) tilt-table subjects.

a) Doppler Indexes, Normalized Percent Change

| | Head Up | Head Down |
|---|---|---|
| $E_{peak}$ (m/s) | −24 ± 17[a] | +4 ± 14[b] |
| AT (s) | +10 ± 12[a] | −9 ± 13[a] |
| DT (s) | +3 ± 18[d] | −7 ± 17[a] |
| $E_{dur}$ (s) | +7 ± 10[a] | −7 ± 11[a] |
| $A_{peak}$ (m/s) | −2 ± 20[a] | +6 ± 15[a] |
| $A_{dur}$ (s) | +0. ± 13[e] | −5 ± 10[a] |
| E/A | −26 ± 20[a] | −5 ± 20[c] |
| HR (beats/min) | +15 ± 9[a] | +8 ± 9[a] |

Data as mean ± standard deviation.
[a] p < 0.0001;
[b] p < 0.001;
[c] p < 0.01;
[d] p = 0.03;
[e] p = 0.09.
All p values vs. baseline.

b) PDF Parameters, Normalized Percent Change

| | Head Up | Head Down |
|---|---|---|
| $C \cdot 10^3$ (1/s) | −33 ± 31[a] | +25 ± 48[a] |
| $K \cdot 10^3$ (1/s$^2$) | −37 ± 16[a] | +19 ± 28[a] |
| $x_o$ (m) | −5 ± 26[b] | +5 ± 26[c] |

Data as mean ± standard deviation.
[a] p < 0.0001;
[b] p = 0.4;
[c] p = 0.07.
All p values vs. baseline.

Example 4

Figure 4:
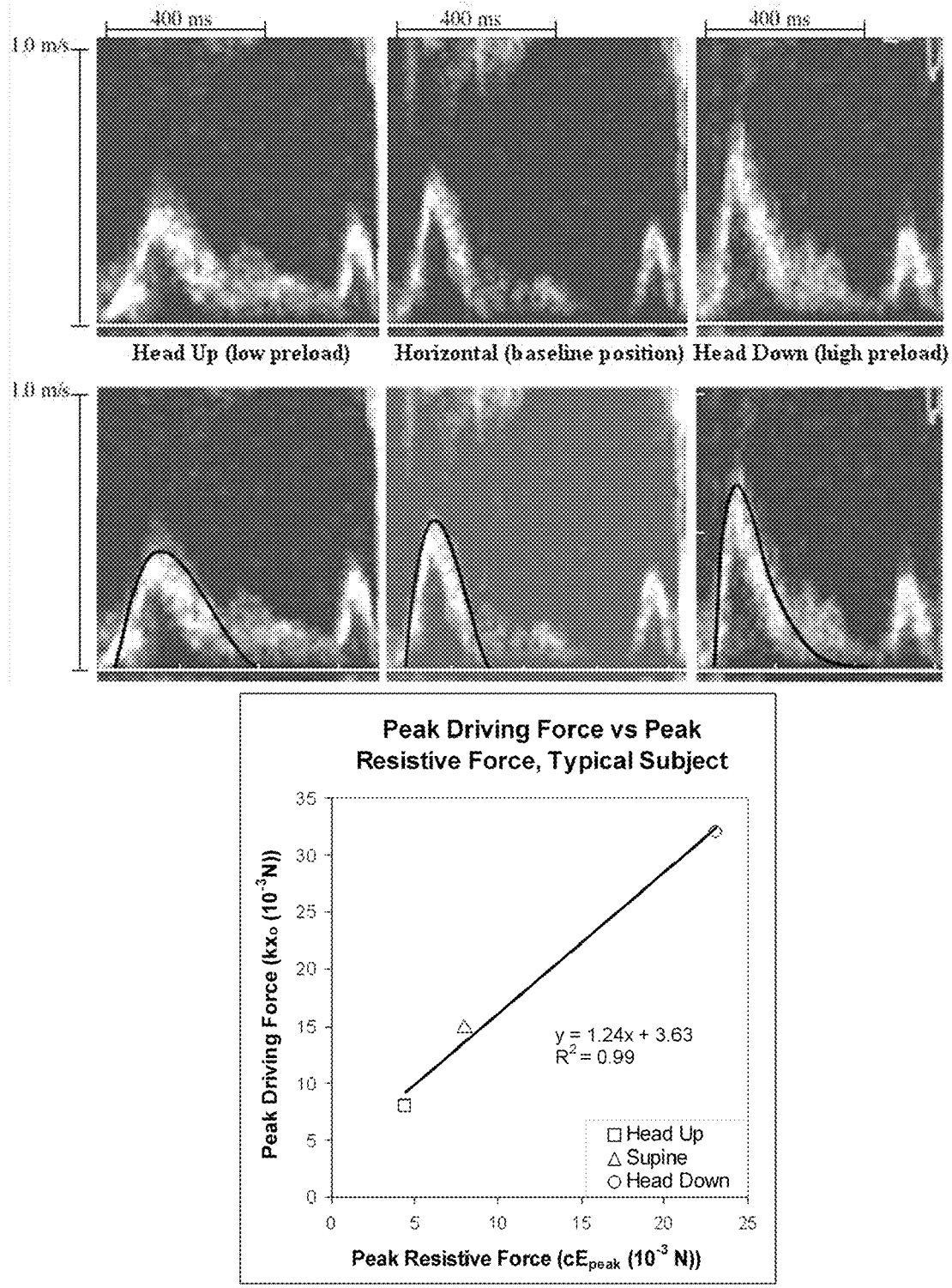
FIG. 4, top row, shows Doppler Waves taken from one subject in (left to right) head up, supine and head down load conditions.

Another benefit of the PDF model is that it allows quantitative rather than qualitative studies to be undertaken. Physiologic information hidden in the images can be extracted from the equations that define the images. This benefit is clearly seen in the tilt table data since a visual inspection of the E-waves from a single subject under different load conditions does not offer much insight while the relationship derived from the parameters k, $x_o$ and c reveals a striking relationship. The top row of FIG. 4 presents three panels showing Doppler Waves recorded from one subject in (left to right) head up, supine and head down load conditions. The bottom panel is a graph of maximum driving force ($kx_o$) vs. peak-resistive force ($cE_{peak}$) derived by extracting the parameterized diastolic filling (PDF) parameters k, $x_o$ and c from E waves in the Doppler data. The graph reveals a strong linear relationship.

FIG. 4, top row, shows Doppler Waves taken from one subject in (left to right) head up, supine and head down load conditions; bottom panel, The waves from the subject in the top row are fit by the PDF formalism, which allows extraction of PDF variables k, $x_o$, and $c$, and allows for a LIIDF to be calculated. While the top panel shows E-wave variation, the bottom panel reveals that the slope and intercept of the $kx_o$ vs $cE_{peak}$ line is constant despite changes in load.

Example 5

The experimental tilt-table derived results show the existence of a load-independent linear relationship between maximum driving force (peak AV gradient $kx_o$) and peak resistive force ($cE_{peak}$). One issue is whether the damped-SHO model itself requires that maximum driving force (peak AV gradient $kx_o$) vs. peak resistive force ($cE_{peak}$) relation must always be linear. To address this issue, random values of k, $x_o$ and c were selected to create E-waves with the requirement that their amplitudes and durations fall within the range of values that have been previously observed and used to fit Doppler data via the PDF formalism. If the observations were a tautology, these E-waves would show a linear relationship between k, $x_o$ and c. The graph of maximum driving force (peak AV gradient $kx_o$) vs. peak resistive force ($cE_{peak}$) using such random values (within the physiologic range) is shown in FIG. 5.

Figure 5:
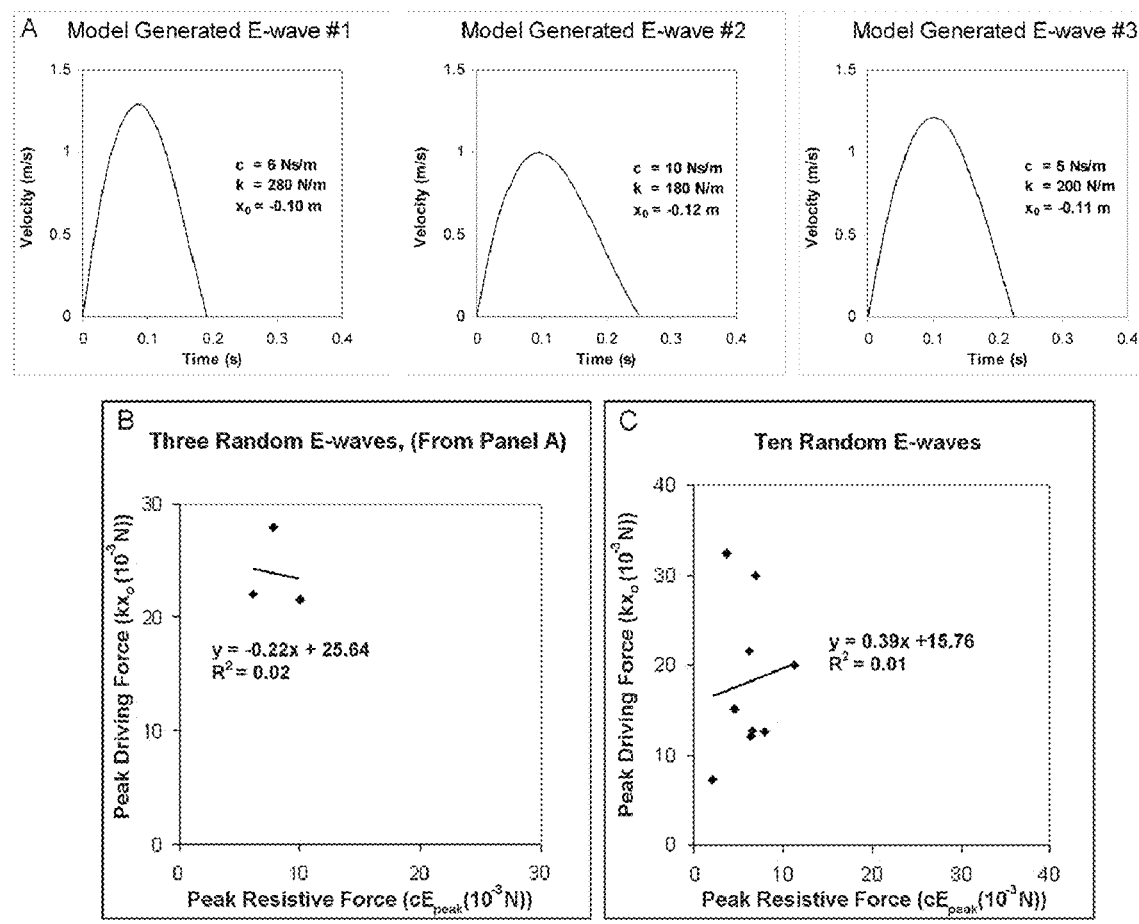
FIG. 5 A) shows three typical model-generated E waves created by randomly picking values for $x_o$, c, k, known to be in the physiologic range.

FIG. 5 shows that not all values of k, $x_o$ and c generate a linear relationship between maximum driving force (peak AV gradient $kx_o$) and peak resistive force ($cE_{peak}$). Therefore the observed linear relation between maximum driving force ($kx_o$) and peak resistive force ($cE_{peak}$) is not a general property of a damped spring model assembled from arbitrary components. Furthermore, the range of values of k, $x_o$ and c that satisfy the maximum driving force (peak AV gradient $kx_o$) vs. peak resistive force ($cE_{peak}$) relationship for a particular heart represents the physiologic regime in which that heart's filling attributes reside.

FIG. 5 A) Three typical model-generated E waves created by randomly picking values for $x_o$, c, k, known to be in the physiologic range.

FIG. 5 B) Maximum driving force ($kx_o$) vs. peak resistive force ($cE_{peak}$) for the three random E-waves shown in a). Note deterioration of $r^2$.

FIG. 5 C) Increase in randomly generated E-wave sample size to n=10 indicates further, substantial deterioration ($r^2=0.01$) of the observed, highly linear, maximum driving force ($kx_o$, peak AV gradient) to peak resistive force ($cE_{peak}$) relationship.

It should be noted that k, c, and $x_o$ are, from a mathematical standpoint, independent parameters. There is therefore no a-priori correlation between k, c, $x_o$, or any combination of the parameters that can be predicted. These parameters become physiologically coupled, and their magnitudes are constrained, once they are fit to clinical data (the E-wave). Once determined by fitting to actual E-waves, several correlations can be seen, such as $E_{peak}$ to $kx_o$, k to $cE_{peak}$, and c to $kx_o$. However, $kx_o$ to $cE_{peak}$ is the strongest observed correlation, and is the only one with a dimensionless slope amenable to a simple physiological interpretation.

Example 6

Validation of Slope M in Subjects with Diastolic Dysfunction

The load-dependence of Min subjects with and without diastolic dysfunction undergoing diagnostic catheterization was tested. This additional analysis used existing data from previous studies (L Bauman et al. "The peak atrioventricular pressure gradient to transmitral flow relation: kinematic model prediction with in-vivo validation.", *J Am Soc Echocardiogr* 8:839-844, (2004); J B Lisauskas et al. "Chamber properties from transmitral flow: prediction of average and passive left ventricular diastolic stiffness.", *J Appl Physiol* 91: 154-162 (2001)) utilizing the Cardiovascular Biophysics Laboratory database of subjects undergoing simultaneous Doppler echocardiographic transmitral flow and micromanometric (Millar) catheter-derived intraventricular (LV) pressure. The database stores simultaneously acquired E-wave transmitral flow velocity contours and high fidelity left ventricular pressures (LVP). The load, defined as the LV end diastolic pressure (LVEDP), is the LVP at the end of the A-wave, before isovolumic contraction. It is important to note that the original intent of the Cardiovascular Biophysics Laboratory database was not explicit testing of load-dependence.

The acquisition of simultaneous echocardiographic-catheterization data has been described previously ((L Bauman et al. "The peak atrioventricular pressure gradient to transmitral flow relation: kinematic model prediction with in-vivo validation.", J Am Soc Echocardiogr 8:839-844, (2004); J B Lisauskas et al. "Chamber properties from transmitral flow: prediction of average and passive left ventricular diastolic stiffness." J Appl Physiol 91: 154-162 (2001)). Briefly, after appropriate sterile skin prep and drape, local anesthesia (1% xylocaine) is administered and percutaneous right or left femoral arterial access is obtained using a valved sheath (6-F, Arrow, Reading, Pa.). A 6-F micromanometer-tipped pigtail pressure-volume (conductance) catheter (Millar Instruments, Houston, Tex., Model SPC 562) is directed into the mid-LV in a retrograde fashion across the aortic valve under fluoroscopic control. Prior to insertion, the manometer-tipped catheter is calibrated against hydrostatic "zero" pressure by submersion just below the surface of a normal saline bath. It is balanced using a transducer control unit (Model TC-510, Millar Instruments, Houston, Tex.). The ventricular pressures are fed to the catheterization laboratory amplifier (Quinton Diagnostics, Bothell, Wash.), and output simultaneously into the auxiliary input port of the Doppler imaging system (Acuson, Mountain View Calif.) and into a digital converter connected to a customized PC. With the subject supine, apical four-chamber views are obtained by the sonographer with the sample volume gated at 1.5 to 2.5 mm and directed between the tips of the mitral valve leaflets orthogonal to the MV plane. To synchronize the hemodynamic and Doppler data, a fiducial marker in the form of a square wave signal is fed from the catheter transducer control unit to both the echocardiographic imager and the PC. Approximately 25 to 50 beats of continuous, simultaneous transmitral Doppler and LV pressure signals are recorded on the imager's magneto-optical disk. Images of individual beats are captured from the disk for offline analysis using custom image processing software.

While subjects underwent no procedures to vary load (i.e. cath table re-positioning, blood pressure cuff procedures, Valsalva, IVC balloon occlusion, fluid challenge, pharmacologic intervention to change load, etc.), some subjects had significant beat-to-beat load variation as well as variation of simultaneously recorded E-wave contours during normal respiration. In these subjects the data were suitable for determination of the $kx_o$ to $cE_{peak}$ relationship as a function of load, i.e. varying LVEDP.

Subjects who had good quality E-waves as well as significant load variation (LVEDP variation >10 mmHg) in response to the respiratory cycle were selected. Selection criteria for inclusion in the diastolic dysfunction group required: normal sinus rhythm, no evidence of valvular disease, no active ischemia, normal ejection fraction (EF)>60% (normal systolic function), and elevated LVEDP (>19 mmHg). Subjects in the control group had: normal sinus rhythm, no valvular disease, no active ischemia, normal EF>60% and normal LVEDP. Because subjects are referred for catheterization to establish the presence of coronary artery disease, variable degrees of CAD were present in both the control and diastolic dysfunction groups. However, no subject in either group had ongoing or active ischemia. Demographics are presented in Table 4. For each subject, 25 consecutive E-waves and simultaneous left ventricular pressures (LVP) were analyzed. Since subjects had significant load variation with respiration, these 25 consecutive E-waves represent the velocity filling profile at varying load states. For each subject, good quality E-waves were selected and analyzed using the MBIP procedure described above. LVEDP (load) was determined from the simultaneous LVP data. The maximum driving force (peak AV gradient $\propto kx_o$) to peak resistive force ($cE_{peak}$) relationship from E-waves as a function of load, defined by beat-to-beat LVEDP variation, was calculated. The linearity of the $kx_o$ to $cE_{peak}$ relationship as a function of LVEDP in this data set, as well as the ability of the slope of the linear regression relationship (M) to differentiate between DD and control states was calculated. The results, including statistics are summarized in FIG. 6 and Table 5.

Figure 6:
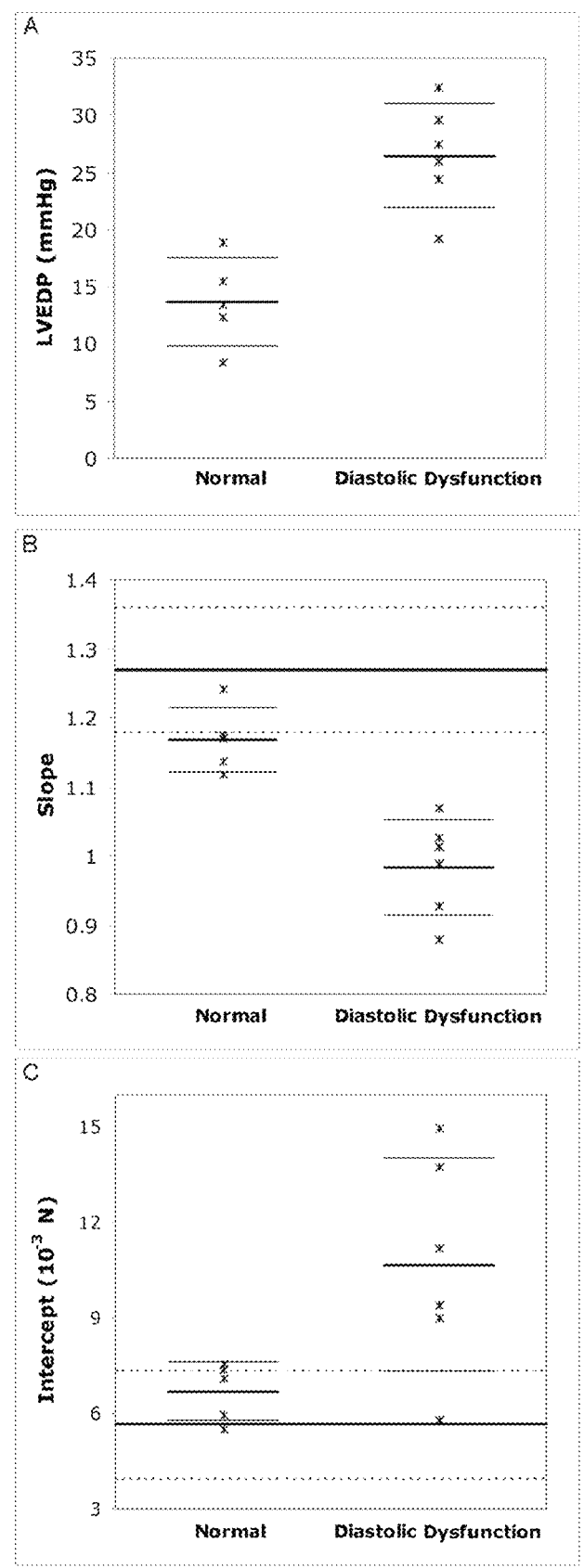
FIG. 6, shows summary comparison of the slope M, and intercept B for all (n=27) subjects comprised of a tilt-table group (n=16) and of a cath-echo group (n=11)

FIG. 6, Summary comparison of the slope M, and intercept B for all (n=27) subjects comprised of a tilt-table group (n=16) and of a cath-echo group (n=11).

FIG. 6 A) The heavier lines denote average values, lighter lines above and below denote one standard deviation relative to the mean LVEDP.

FIG. 6 B) Regression slope (M) comparison between groups. The thick-line is the average value from the tilt-table study. Dotted lines are one standard-deviation relative to the mean value.

FIG. 6 C) Intercept (B) comparison between groups. The thick-line is average value from the tilt-table study. Dotted lines are one standard deviation relative to the mean intercept value.

TABLE 4

Demographics of Simultaneous Catheterization-echocardiography Subjects Analyzed Retrospectively

|  | Control (n = 5) | Diastolic Dysfunction (n = 6) |
| --- | --- | --- |
| Age | 44 ± 9 | 49 ± 13 |
| Weight | 156 ± 30 | 202 ± 48 |
| Systolic LV Pressure | 119 ± 8 | 147 ± 25[a] |
| Ejection Fraction | 73 ± 8 | 68 ± 8 |
| LVEDP | 13 ± 4 | 26 ± 5[b] |

Data is mean ± standard deviation.
[a]$p < 0.05$;
[b]$p < 0.001$;
p values calculated by ANOVA

TABLE 5

Results for Prospective Tilt Table and Retrospective Cath-Echo Studies.

|  | Echo-Cath Normals | Echo-Cath Diastolic Dysfunction | Tilt Table Normals |
| --- | --- | --- | --- |
| LVEDP (mmHg) | 13.69 ± 3.87[a] | 26.47 ± 4.54 |  |
| Slope (M) | 1.17 ± 0.05[b] | 0.98 ± 0.07[d] | 1.27 ± 0.09 |
| Intercept (B) | 6.69 ± 0.91[c] | 10.67 ± 3.35[e] | 5.69 ± 1.70 |
| $r^2$ | 0.96 ± 0.02 | 0.90 ± 0.05 | 0.95 ± 0.04 |

Data shown as mean ± standard deviation. Single Paired ANOVA performed between echo-cath normals and echo-cath diastolic dysfunction subjects as well as between echo-cath subjects and tilt table subjects.
[a]$p < 0.001$;
[b]$p < 0.001$ compared to diastolic dysfunction, p = 0.02 compared to tilt table;
[c]p = 0.03 compared to diastolic dysfunction, p = 0.22 compared to tilt table;
[d]$p < 0.00001$ compared to tilt table;
[e]$p < 0.001$ compared to tilt table.

The $kx_o$ vs $cE_{peak}$ relation was highly linear for both normal (average $r^2$=0.96±0.02) and diastolic dysfunction groups (average $r^2$=0.90±0.05). The average slope for the normal group was M=1.17±0.05, and the average value for the diastolic dysfunction group was M=0.98±0.07, p<0.001 by ANOVA. Additionally, the slope intercept of the normal cath-echo group was B=6.69±0.91, while the slope intercept of the diastolic dysfunction cath-echo group was B=10.67±3.35, p=0.03 by ANOVA. The difference in M between the cath-echo diastolic dysfunction subjects and the healthy tilt-table subjects showed stronger statistical significance (p<0.00001) compared to the difference in M between the cath-echo normal subjects and the healthy tilt-table subjects (p=0.02). The difference in intercept B is also statistically significant between diastolic dysfunction subjects and tilt-table subjects, p<0.0001. There was no statistically significant difference between the intercept of the normal cath-echo subjects and the tilt-table subjects.

FIG. 6 provides compelling evidence that both slope M and intercept B change in LV diastolic dysfunction states. The diastolic dysfunction group had lower M values and higher B values compared to the normal cath-echo group and the healthy tilt-table group [Example 1]. The normal cath-echo group had the same B values as the healthy tilt-table group and slightly lower M values. This difference in M between the normal cath-echo subjects and the tilt-table subjects may be due to the higher average age of the normal cath-echo subjects (44 yo) relative to the healthy tilt-table group (25 yo).

These preliminary data, particularly because they were not acquired with the specific intent of determining load independence, strongly support the view that M and B can differentiate between normal and pathologic states. Because M is the slope of a regression relation, it provides relative information regarding the efficiency with which the ventricle adapts to load.

Example 7

Figure 7:
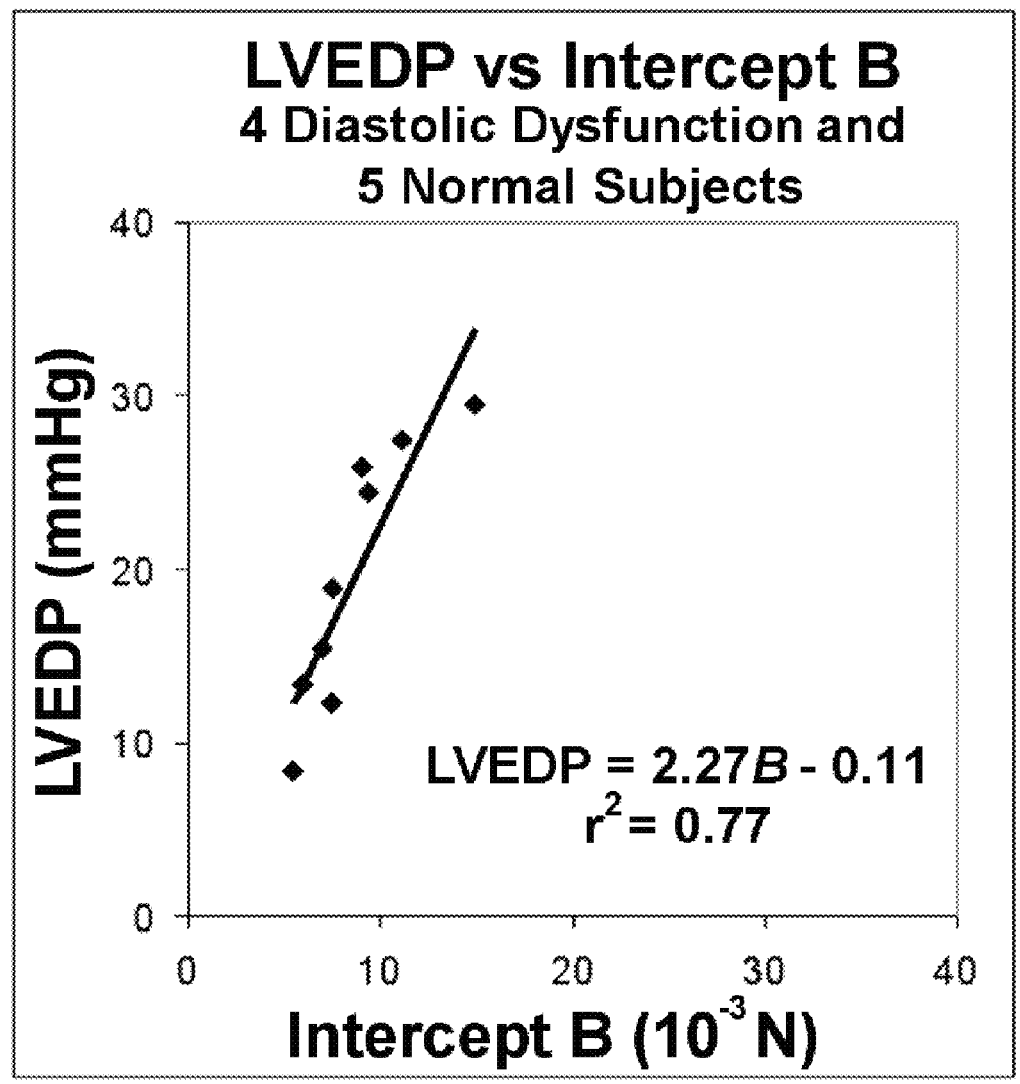
FIG. 7 presents data from 9 subjects, 4 with isolated diastolic dysfunction and 5 normal controls.

In the previous example both the slope and intercept of the $kx_o$ vs $cE_{peak}$ plot were significantly different in patients with diastolic dysfunction compared to patients without diastolic dysfunction. While the slope (M) represents a LIIDF that provides relative information regarding the efficiency with which the ventricle adapts to load, the intercept (B) is also uniquely determined despite load variation and must be determined by left ventricular parameters. While the slope (M) is dimensionless, the vertical intercept (B) has units of force, or equivalently pressure. Thus it is intriguing to consider the possibility that the vertical intercept (B) embodies pressure related information. Additionally, it was clearly demonstrated in the previous EXAMPLE that patients with high LVEDP and diastolic dysfunction had significantly higher vertical intercept values compared to normal controls with normal LVEDP. In fact, the noninvasive vertical intercept (B) of the $kx_o$ vs $cE_{peak}$ relation shows a strong linear correlation ($r^2$=0.77) with the invasively-derived average operating LVEDP in preliminary results for 9 subjects (4 with diastolic dysfunction, 5 normal controls). (FIG. 7). This correlation is impressive given that all subjects had normal ejection fraction (>50%), and other methods for noninvasive estimation of operating left ventricular pressure have proven to be less reliable in patients with normal ejection fractions (Yamamoto K et al. "Determination of left ventricular filing pressure by Doppler echocardiography in patients with coronary artery disease: critical role of left ventricular systolic function." *Journal American College of Cardiology* 30(7):1819-1826 (1997)). Thus, by determination of the vertical-intercept of the maximum driving force to peak resistive force relationship, a clinician can non-invasively estimate the average operating LVEDP, which is an invasively acquired index. More importantly, a clinician can determine if the LVEDP is increasing or decreasing in the same patient by determining the intercept of the maximum driving force to peak resistive force ($kx_o$ vs $cE_{peak}$) relationship over sequential echocardiographic studies.

FIG. 7 presents data from 9 subjects, 4 with isolated diastolic dysfunction and 5 normal controls. All subjects had significant respiratory variation. E-waves were acquired from various load states, $kx_o$ and $cE_{peak}$ were calculated for each wave, and the resulting $kx_o$ values were plotted against $cE_{peak}$. The slope M and intercept B of the $kx_o$ vs $cE_{peak}$ relationship was calculated for each subject. The FIGURE presents the average left ventricular end diastolic pressure (LVEDP) vs vertical intercept B for the 9 subjects. The strong linear relationship allows for the noninvasive estimation of left ventricular operating pressures by the intercept B.

Example 8

The previous examples demonstrate the utility of the load independent index M, but they all rely on fitting Doppler E-waves by the PDF formalism. While mathematically this is the most exact approach, it is currently not the most clinically widespread because the PDF formalism is not available on all echo machines. Hence in day-to-day clinical practice, analysis of E-waves performed by sonographers and physicians relies on visual analysis and simple triangular or similar mathematically smoothed approximations to the E-wave's shape. The middle and bottom panels of FIG. 2 shows a typical E-wave fit by the PDF formalism and by the simple triangle approximation that is in current clinical use. In approximating the E-wave by a triangle, the entire profile becomes defined by the acceleration time, deceleration time, and peak height of the wave (AT, DT, and $E_{peak}$ respectively). In addition, $E_{peak}$, DT and AT, and combinations of these variables and other geometrically derived indices, are used in clinical practice to differentiate between normal and abnormal heart function states.

The triangular approximation for E-wave shape (AT, DT, $E_{peak}$) is the 'language' that clinicians currently use for the analysis of Doppler E-waves. As such, a derivation and validation of the load independent index M, using the 'language' of the simple triangular approximation, would serve as independent support for the physiologic basis and clinical utility of M that could be easily understood by clinicians and sonographers. Such a derivation is possible, and while it does not rely on or use any PDF variable, insights provided by kinematic modeling are used as a guide in determining which E-wave shape-based measures reflect the physiology relating the peak pressure gradient to peak resistive force.

The starting motivation is the fundamental equation of motion per unit mass for the PDF formalism discussed in example 1.

$$\frac{d^2x}{dt^2} + c\frac{dx}{dt} + kx = 0 \quad [6]$$

At the time of peak velocity, where the acceleration $d^2x/dt^2$ vanishes, the following identity applies:

$$cE_{peak} = kx(t_{peak}) \quad [7]$$

In addition, considering equation [6] at the initial time t=0 where the velocity dx/dt vanishes, the following identity applies:

$$d^2x/dt^2 = kx_o \quad [8]$$

Thus, the maximum driving force ($kx_o$) is exactly equal to the maximum initial upslope of the velocity profile. The initial upslope of the velocity profile can be approximated by purely geometric means (using only commonly used geometric parameters $E_{peak}$, AT, and DT) (see FIG. 8), namely $$d^2x/dt^2|_{t=0} = E_{peak}/AT \quad [9]$$

Thus the geometric equivalent maximum driving force ($kx_o$) is approximated by $E_{peak}/AT$.

Figure 8:
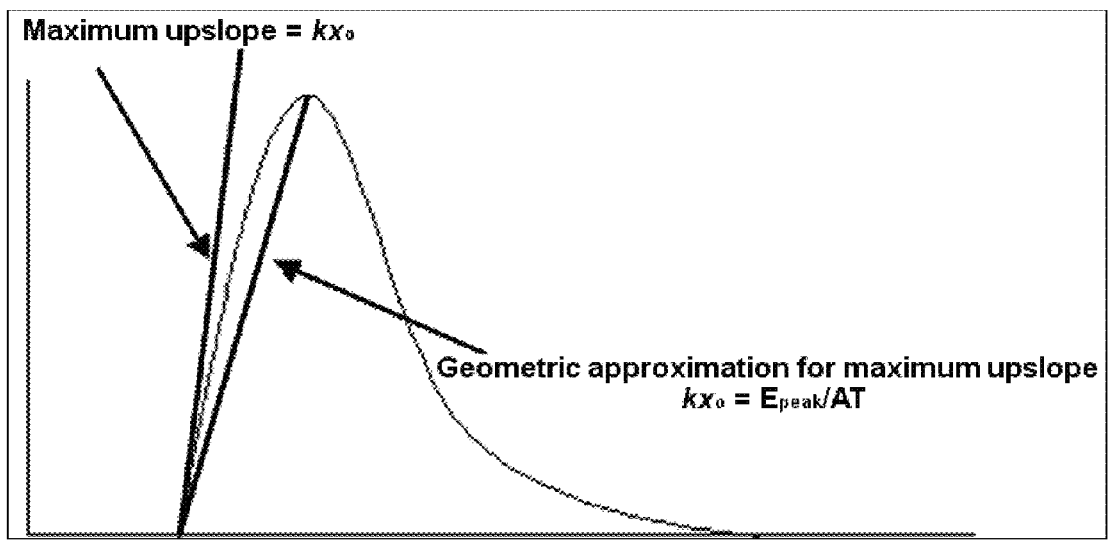
FIG. 8 shows the basis for the geometric approximation of $kx_o$.

FIG. 8 shows the basis for the geometric approximation of $kx_o$. Mathematical analysis reveals that $kx_o$ is exactly equal (for any wave) to the maximum upslope of the velocity contour. The closest approximation for the maximum upslope using accepted geometric parameters ($E_{peak}$, AT, DT) is $E_{peak}/AT$. This approximation will always underestimate the true slope, and becomes better with decreasing AT.

To derive the geometric equivalent peak resistive force, a geometric approximation to $kx_{peak}$ must be found, which by equation [7] is equal always to $cE_{peak}$. For this derivation, the solution of equation [6] for the displacement yields:

$$x = x_o e^{-\alpha t}\left(\cos(\omega t) + \frac{\alpha}{\omega}\sin(\omega t)\right) \quad [10]$$

$$\omega = \frac{\sqrt{4k - c^2}}{2}, \alpha = \frac{c}{2}$$

The time at which the displacement vanishes (x=0) is:

$$\frac{\alpha}{\omega} = -\frac{\cos(\omega t)}{\sin(\omega t)} \quad [11]$$

$$\omega t = a\tan\left(-\frac{\omega}{\alpha}\right)$$

$$\frac{\pi}{\omega} - \frac{1}{\omega}a\tan\left(\frac{\omega}{\alpha}\right) = t|_{x=0}$$

The velocity of the E-wave, given by the derivative of [10] is:

$$v(t) = k x_o e^{-\alpha t}(\sin(\omega t)) \quad [12]$$

The acceleration time of the wave can be found by finding the time at which the derivate of the velocity vanishes:

$$0 = kx_o(-\alpha e^{-\alpha t}\sin(\omega t) + \omega e^{-\alpha t}\cos(\omega t)) \quad [13]$$

$$t_{AT} = \frac{1}{\omega}a\tan\left(\frac{\omega}{\alpha}\right)$$

The duration of the wave is given by finding the time where the velocity vanishes:

$$v(t) = kx_o e^{-\alpha t}(\sin(\omega t)) \quad [14]$$

$$t|_{v=0} = \frac{\pi}{\omega}$$

Thus the deceleration time of the wave is given by the difference of E-wave duration [9] and E-wave acceleration time [8]:

$$DT = \frac{\pi}{\omega} - \frac{1}{\omega}a\tan\left(\frac{\omega}{\alpha}\right) \quad [15]$$

This is exactly the time at which the displacement x vanishes by equation [11].

Since the initial displacement is by definition $x_o$, the initial displacement is also given by the area under the velocity contour from t=0 to t=DT. Additionally, the displacement at the peak velocity, $x_{peak}$, is given by the area under the velocity contour from t=AT to t=DT (FIG. 9).

Figure 9:
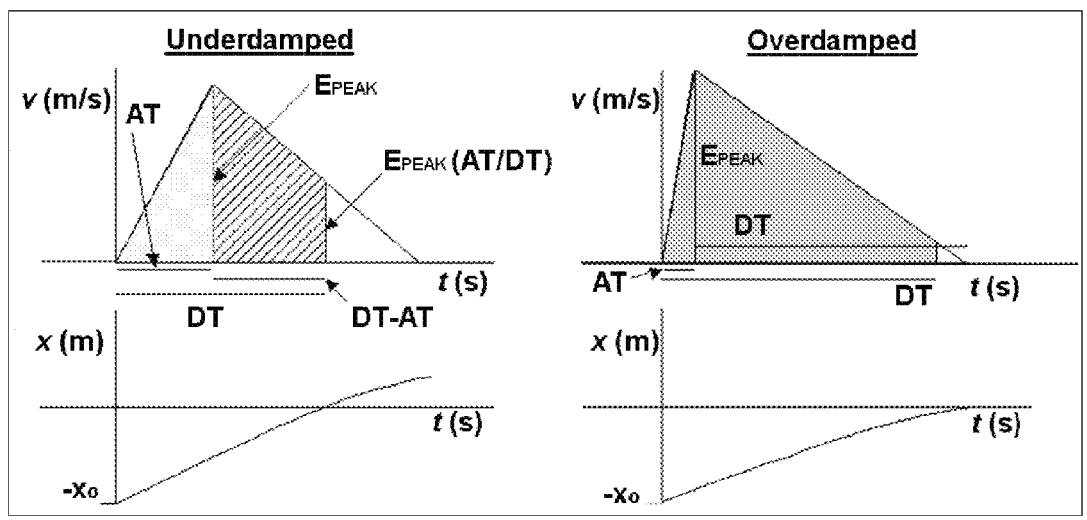
FIG. 9 shows the basis for the $x_o$ and $x_{peak}$ approximation.

FIG. 9 shows the basis for the $x_o$ and $x_{peak}$ approximation. The left panel shows a triangular approximation to an underdamped wave. The right panel shows a triangular approximation to an overdamped wave. Mathematical analysis of underdamped waves reveals that the displacement of the PDF spring which moves with the velocity of the E-wave vanishes (x=0) at a time t=DT, where DT is the deceleration time of the E-wave. Thus, the area under the velocity contour (E-wave) from t=0 to t=DT (shaded green) is exactly equal to $x_o$. Similarly, the area under the E-wave from t=AT to t=DT (striped area) is exactly equal to $x_{peak}$. To approximate this area geometrically, the total curved area is approximated as being triangular. For overdamped waves, the displacement becomes exceedingly small as the velocity approaches zero. Thus the area from t=0 to t=DT will be close to the entire area of the E-wave, and will approximate $x_o$ well.

Thus, an approximation for $x_o$ using the commonly employed geometric indexes $E_{peak}$, AT, and DT, is $$x_o = \frac{E_{peak} AT}{2} + \frac{E_{peak}}{2}\left(1 + \frac{AT}{DT}\right)(DT - AT) \quad [16]$$

Similarly, an approximation for $x_{peak}$ using the commonly employed geometric indexes $E_{peak}$, AT, and DT, is:

$$x_{peak} = \frac{E_{peak}}{2}\left(1 + \frac{AT}{DT}\right)(DT - AT) \quad [17]$$

Thus, incorporating equation [9], [16], [17] produces:

$$kx_o = \frac{E_{peak}}{AT} \quad [18]$$

$$cE_{peak} = kx_{peak} = kx_o \cdot \frac{x_{peak}}{x_o}$$

$$cE_{peak} = \frac{E_{peak}}{AT} \cdot \frac{\frac{E_{peak}}{2}\left(1 + \frac{AT}{DT}\right)(DT - AT)}{\frac{E_{peak} AT}{2} + \frac{E_{peak}}{2}\left(1 + \frac{AT}{DT}\right)(DT - AT)}$$

Finally, the geometric equivalent peak resistive force $cE_{peak}$ expression can be simplified to:

$$cE_{peak} = \frac{E_{peak}}{AT} \frac{DT^2 - AT^2}{(DT^2 - AT^2 + AT \cdot DT)} \quad [19]$$

Thus the geometric equivalent approximation predicts that the slope of the $$E_{peak}/AT \text{ versus } \frac{E_{peak}}{AT} \frac{DT^2 - AT^2}{(DT^2 - AT^2 + AT \cdot DT)}$$

relation is a load independent index of diastolic function.

FIG. 10 presents a plot of $E_{peak}/AT$ versus $$\frac{E_{peak}}{AT} \frac{DT^2 - AT^2}{(DT^2 - AT^2 + AT \cdot DT)}$$

for one of the control subjects from example 4. Notice that the plot is highly linear ($r^2$=0.99).

Since $E_{peak}$, AT and DT are obtained purely from measuring geometric features of the E-wave, the observed relation reinforces the conclusion that our results are not due to our choice of modeling the kinematics of filling in analogy to a simple harmonic oscillator, but instead reflect fundamental physiology of filling.

Example 9

While a derivation of the LIIDF and the non-invasive estimate of left ventricular operating pressures using the "language of cardiology" as presented in EXAMPLE 6 is highly practical and useful, more refined approximations to the exact PDF value can be made with modification to the geometric methods employed in approximating the E-wave contours. In day-to-day clinical practice, analysis of E-waves performed by sonographers and physicians relies on visual analysis of the E-wave shape, and approximation methods must rely on well-established ability of the sonographers and physicians to measure specific points from the E-wave contours. In the current "language or cardiology" the points of interest of the E-wave are the initial, peak, and end points. These points alone derived from E-waves acquired at different loads can be used to derive the LIIDF and the non-invasive estimate of left ventricular operating pressures as detailed in EXAMPLE 6. The addition of new points of interest to the clinical vocabulary, however, can lead to more refined and accurate estimates of the LIIDF and the non-invasive estimate of left ventricular operating pressure. New points and measures of interest are presented for the E-wave that are easily implemented and represent non model-based approaches to estimating the LIIDF and the noninvasive estimate of left ventricular operating pressure.

Example 10

More Refined Geometric Estimation of the Maximum Driving Force ($kx_o$)

Mathematical analysis reveals that the maximum initial upslope of the E-wave contour is exactly equal to the maximum driving force ($kx_o$). In the current standard practice of cardiology, the maximum E-wave upslope is approximated by $E_{peak}/AT$, but numerous methods exist by which a closer approximation to the maximum upslope can be made. First, once the AT is determined, the user can be asked to measure the amplitude of the E-wave at the midpoint between the peak time and the initial time, in other words at t=AT/2. The amplitude of the E-wave at t=AT/2 is $E_{AT/2}$, and a closer approximation to the maximum upslope of the E-wave is then given by $2E_{AT/2}/AT$ (FIG. 11).

FIG. 11 shows the basis for the geometric refinements in the approximation of $kx_o$. Mathematical analysis reveals that $kx_o$ is exactly equal (for any wave) to the maximum upslope of the velocity contour. If the amplitude of the E-wave is measured at a time t=AT/2, then a close approximation to the maximum upslope of the wave can be achieved by calculating $2E_{AT/2}/AT$. On the other hand, it is possible to implement methods whereby the maximum upslope of the E-wave is measured directly, in which case an exact determination of kxo may be achieved: $kx_o = E_{max\ initial\ upslope}$.

By this methodology $kx_o = 2E_{AT/2}/AT$. On the other hand, a computer interface can draw a line with an endpoint at the initial point of the E-wave that the user can rotate on the screen. If the user is instructed to rotate this line until it is parallel to the maximum initial upslope of the E-wave, then the resulting slope of this user-defined line will be an extremely close approximation to $kx_o$ (FIG. 11).

Closer estimates of $kx_o$ can be used to calculate closer estimates of k, since $x_o$ is $$x_o = \frac{E_{peak}}{2}\left(\frac{DT^2 - AT^2 + AT \cdot DT}{DT}\right)$$

well approximated by as detailed in EXAMPLE 6.

$$x_{peak} = \frac{E_{peak}}{2}\left(\frac{DT^2 - AT^2}{DT}\right),$$

In addition, because $cE_{peak}=kx_{peak}$ and closer estimates of the initial maximum upslope of the E-wave can be used to find closer estimates to $cE_{peak}$:

$$cE_{peak} = E_{max\ initial\ upslope}\left(\frac{DT^2 - AT^2}{DT^2 - AT^2 + AT \cdot DT}\right).$$

Example 11

More Refined Estimation of $cE_{peak}$

The damping parameter c controls the curvature of the wave, especially the curvilinear nature of the deceleration portion of the E-wave. Because the current "language" of cardiology ($E_{peak}$, AT, DT) treats all E-waves as triangles and does not account for the curvature of the E-wave contour, it is not surprising that estimates of c are difficult to achieve. Adding measurements of the E-wave amplitude during the deceleration portion to the "vocabulary" of clinical echocardiography can serve to better capture the curvature of the wave. A particularly useful measurement to make is the amplitude of the E-wave at t=2AT ($E_{2AT}$). For mathematical reasons t=2AT is the inflection point of the E-wave, and therefore it is appropriate to refer to $E_{2AT}$ as the inflection point velocity. Once the user defines AT, and DT by traditional triangle approaches in a suitable user interface that presents the E-wave to the user, the interface can draw a vertical line a distance AT from the peak of the wave and instruct the user to find the intersection point between the drawn vertical line and the E-wave contour. This is merely one method by which the user or program can define $E_{2AT}$, the inflection point velocity.

The inflection point velocity $E_{2AT}$ is relevant because the second derivative vanishes at that point, and mathematical identities can be employed to reveal simple approximations to the parameters c and k. Considering the fundamental equation of motion for the damped SHO:

$$\ddot{x}+c\dot{x}+kx=0 \quad [20]$$

Taking the derivative with respect to time of the equation of motion yields:

$$\dddot{x} + c\ddot{x} + k\dot{x} = 0 \quad [21]$$

If the above equation is evaluated at the inflection point, t=2AT, the third derivative of displacement vanishes, and what remains is a connection between stiffness and damping constant:

$$c = k\frac{v(t)}{\dot{v}(t)}\bigg|_{t=2AT} \quad [22]$$

The measure of the inflection point velocity ($E_{2AT}$), is plugged into the numerator of the above equation. The slope at the inflection point is approximated by a line connecting the inflection point velocity ($E_{2AT}$) and the peak velocity, although an automated method that more correctly fits the E-wave shape may be used for a closer approximation to the slope of the E-wave at the inflection point.

Thus, one geometric formula approximating the damping constant c is:

$$c = k\frac{E_{2AT}}{\frac{E_{peak} - E_{2AT}}{AT}}$$

Using this formula, any geometric approximation can be used for k, including the simple geometric method in EXAMPLE 6, as well as the methods presented in this section based upon determination of the maximum initial upslope of the E-wave ($E_{max\ initial\ upslope}$). Thus, a general expression for a refined geometric approximation for the peak resistive force opposing blood flow ($cE_{peak}$) is:

$$cE_{peak} = E_{peak}\frac{AT \cdot E_{2AT}}{E_{peak} - E_{2AT}}(E_{max\ initial\ upslope})\frac{DT^2 - AT^2}{DT^2 - AT^2 + AT} \quad [23]$$

Example 12

A Refined Method for the Determination of the LIIDF and the Noninvasive Estimate of Left Ventricular Operating Pressure by Geometric Approximations Presented is an embodiment of a method by which more refined estimates of the LIIDF and the noninvasive estimate of left ventricular operating pressure are determined. This embodiment relies on adapting established interfaces used by clinicians and sonographers for measurement of E-wave parameters. First the user defines the initial, final, and peak points of the E-wave, thus determining AT, DT, and $E_{peak}$ (FIG. 12).

FIG. 12 demonstrates one embodiment of the method as implemented in a echocardiographic machine or offline analysis suite. To aid in the determination of parameters necessary for the non model-based calculation of the LIIDF and the noninvasive estimate of left ventricular filling, a first step consists of determining values that are routinely measured in clinical echocardiography by both sonographers and clinicians. A second step details measurements that may be easily made by clinicians and sonographers. The parameters found in the second step can be used to calculate accurate estimates for the LIIDF and the non-invasive estimate of left ventricular filling.

Next the interface superimposes vertical lines at distance AT/2 to the left of the peak point, and at a distance AT to the right of the peak point. Finally the user must determine the point of intersection between the vertical lines and the velocity contour, thus defining $E_{AT/2}$ and $E_{2AT}$ respectively. With the parameters AT, DT, $E_{peak}$, $E_{AT/2}$, and $E_{2AT}$ the interface calculates the geometric maximum driving force ($2E_{AT/2}/AT$) and the geometric peak resistive force opposing flow:

$$\frac{4E_{AT/2} \cdot DT}{(DT^2 - AT^2 + AT \cdot DT)} \frac{E_{2AT}}{E_{peak} - E_{2AT}}.$$

This process is repeated for several E-waves acquired at different loads, and the linear relationship (slope M and vertical intercept B) between $2E_{AT/2}/AT$ and $$\frac{4E_{AT/2} \cdot DT}{(DT^2 - AT^2 + AT \cdot DT)} \frac{E_{2AT}}{E_{peak} - E_{2AT}}$$

is determined. The slope M defines the LIIDF while the vertical intercept B defines the noninvasive estimate of left ventricular operating pressure. FIG. 13 presents a plot of $2E_{AT/2}/AT$ and $$\frac{4E_{AT/2} \cdot DT}{(DT^2 - AT^2 + AT \cdot DT)} \frac{E_{2AT}}{E_{peak} - E_{2AT}}$$

for a typical subject with load variation from respiration alone.

Example 13

The tilt table data, as well as the respiratory variation data as presented and described in the preceding examples show that varying load affects the E-waves and the associated PDF parameters ($k$, $x_o$, and $c$). The observed variation reflects the physiologic compensatory mechanisms that respond to changes in load. The slope of the $kx_o$ vs $cE_{peak}$ relationship is unaltered with alteration of load (as shown, for example, in FIG. 3), which supports the conclusion that the slope represents a load independent measure of diastolic early rapid filling, and is an intrinsic property of diastolic filling that does not change with changes in load.

Physiologic Significance

The $kx_o$ vs $cE_{peak}$ plot reveals physiologic information about how the ventricle adjusts to changes in load. The lower left of the plot is the low load filling regime, while the upper right is the high load filling regime. FIG. 14, panel A is a $kx_o$ vs $cE_{peak}$ graph indicating various load regimes. FIG. 14, panel B is shows two different $kx_o$ vs $cE_{peak}$ lines, one with a high slope and one with a low slope, against the load regimes shown in panel A. Note that for the same increase in peak driving force, seen as an increase in $kx_o$, a ventricle with a high slope has a far smaller (75% smaller) in peak resistive force compared to the ventricle with lower slope. Thus a ventricle with a high slope (M) has less viscous/resistive loss forces for similar increases in load compared to a low $kx_o$ vs $cE_{peak}$ slope (M). Larger M values imply better DF in that increasing A-V pressure gradient results in relatively smaller increases in peak resistive losses ($cE_{peak}$). Conversely, lower M implies that increasing A-V gradient leads to larger increases in resistive losses ($cE_{peak}$).

FIG. 14 shows $kx_o$ vs $cE_{peak}$ graphs indicating different load regimes. The left panel shows low load, supine load, and high load regimes. The panel on the right presents theoretical lines derived from different ventricles. Notice that the same increase in peak driving force (correlated with increases in load) results in far less increase in peak resistive force for ventricles with high slope compared to ventricles with low slope. Thus the ventricle with higher slope is able to adjust to different filling regimes with less energy losses and therefore more efficiency compared to ventricles with lower slopes.

Example 14

Physiologic Prediction

Interestingly, only certain regimes of the maximum driving force (peak AV gradient $kx_o$) vs. peak resistive force ($cE_{peak}$) graph can exist physiologically. Energy conservation makes it impossible for $cE_{peak}$, the peak resistive force opposing filling, to exceed $kx_o$, the initial (and maximum) driving force initiating filling. If M is low, specifically <1, as load increases, the maximum driving force (peak AV gradient $kx_o$) vs. peak resistive force ($cE_{peak}$) regression line approaches the $kx_o = cE_{peak}$ boundary, eventually crossing it and moving into the non-physiologic regime. A ventricle having M<1 would therefore not be able to maintain filling function in the face of increased load (FIG. 15).

FIG. 15 is a graph of Peak Driving Force versus Peak Resistive Force illustrating physiological constraints governing filing. The Equation governing filling (Eq [1]) constrains the physiology to the upper half of the plot because the peak resistive force ($cE_{peak}$) can never exceed the peak driving force ($kx_o$). A chamber with M<1 operates on a regression line that may eventually reach the prohibited regime for sufficiently elevated peak driving force (AV gradient) values. In contrast, a chamber having M>1 is not similarly constrained.

In examples supra it was shown that the vertical intercept B of the maximum driving force ($kx_o$) vs. peak resistive force ($cE_{peak}$) relation could also be considered as conveying a noninvasive estimate of left ventricular operating pressures because it is highly correlated with invasively derived LVEDP. Such an interpretation for the vertical intercept B suggests the comparison in FIG. 16, with two $kx_o$ vs $cE_{peak}$ lines: both lines have equal slopes M, but one has significantly higher vertical intercept than the other. As the physiologic load of each ventricle changes, the resulting E-wave will inhabit different positions on their respective $kx_o$ vs $cE_{peak}$ lines. Since the area below the diagonal is not physiologically allowed, it is clear that the regime of load variation available to the ventricle with lower intercept is more restricted than the regime of load variation available to the ventricle with higher vertical intercept. Thus, a natural compensatory mechanism for having a ventricle with low dynamic diastolic filling efficiency M is to push the vertical intercept, and therefore the operating LVEDP, to a higher value. Indeed, a ventricle with a low M and low vertical intercept B would be in more danger of crossing the non-physiologic regime on the right side of FIG. 16 with fluctuations in load than a ventricle with a similarly low M but high vertical intercept B. In fact a linear relationship exists between M and B when all mentioned subjects from the examples supra are considered (FIG. 17). A continuously increasing B with decreasing M demonstrates that the compensatory mechanism is one that applies for heart with normal and abnormal diastolic function.

FIG. 16 is a graph of Peak Driving Force versus Peak Resistive Force and two limits for a ventricle with low slope. In light of the physiological restriction demonstrated in FIG. 16, it is natural to consider two limits for ventricle with low slope: ventricles with low slope and low intercept and ventricles with low slope and high intercept. Ventricles with low slope, specifically M<1, reach a forbidden regime of filling with increases in load. By raising the intercept to a higher value, a ventricle with low slope will have a larger physiology regime of load changes that are allowed. Thus higher intercept B serves as a compensatory mechanism to increase the physiologically allowed regime of load variation.

FIG. 17 shows the relationship between the LIIDF (M) and the noninvasive estimate of left ventricular operating pressure (B) for 26 subjects (15 heart healthy subjects undergoing tilt table variation, 6 cath-echo patients with diastolic dysfunction and 5 cath-echo control patients). M and B values were calculated from cath-echo patients through respiratory variation induced load changes. As predicted, ventricles with poorer diastolic function, as evidenced by decreased M values, had higher noninvasive estimates for left ventricular operating pressures (B). The strong ($r^2$=0.75) linear relationship demonstrates that a consequence of diastolic dysfunction is increased filling pressures.

REFERENCES CITED

All references cited in the present application are incorporated herein by reference in their entirety and for all purposes to the same extent as if each individual publication, patent or patent application was specifically and individually indicated to be incorporated by reference in its entirety for all purposes. Citation of a reference herein shall not be construed as an admission that such is prior art to the present invention.

REFERENCES

J. Sztajzel et al., "Effect of altered loading conditions during haemodialysis on left ventricular filling pattern", Eur Heart J. 1993 14(5):655-61.

Hurrell D G, et al., "Utility of preload alteration in assessment of left ventricular filling pressure by Doppler echocardiography: a simultaneous catheterization and Doppler echocardiographic study.", J Am Coll Cardiol. 1997 August, 30(2):459-67.

Triulzi M O, et al., "Effects of preload reduction on mitral flow velocity pattern in normal subjects.", Am J Cardiol. 1990 Oct. 15; 66(12): 995-1001.

Masuyama T., et al., "Effects of nitroprusside on transmitral flow velocity patterns in extreme heart failure: a combined hemodynamic and Doppler echocardiographic study of varying loading conditions.", J Am Coll Cardiol. 1990 November; 16(5):1175-85.

Plotnick G D, et al., "Effect of autonomic blockade, postural changes and isometric exercise on Doppler indexes of diastolic left ventricular function.", Am J Cardiol. 1991 Jun. 1; 67(15):1284-90.

Schwengel R H, et al., "Abnormal Valsalva blood pressure response in dilated cardiomyopathy: association with "pseudonormalization" of echocardiographic Doppler transmitral filling velocity pattern.", Am Heart J. 1993 November; 126(5):1182-6.

Yamamoto K, et al., "Peak early diastolic filling velocity may decrease with preload augmentation: effect of concomitant increase in the rate of left atrial pressure drop in early diastole.", J Am Soc Echocardiogr. 1993 May-June; 6(3 Pt 1):245-54.

Stoddard M F, et al., "Influence of alteration in preload on the pattern of left ventricular diastolic filling as assessed by Doppler echocardiography in humans.", Circulation. 1989 June; 79(6):1226-36.

Voller H, Spielberg C, et al., "Doppler echocardiography measurement of diastolic filling parameters in acute changes of pre- and afterload in healthy probands", Z Kardiol. 1992 December; 81(12):687-94.

Suzuki T, et al., "Influence of postural change on transmitral flow velocity profile assessed by pulsed Doppler echocardiography in normal individuals and in patients with myocardial infarction.", Am Heart J. 1990 July; 120(1):110-5.

Garcia M J, et al., "Color M-mode Doppler flow propagation velocity is a preload insensitive index of left ventricular relaxation: animal and human validation.", J Am Coll Cardiol. 2000 January; 35(1):201-8.

Garcia M J, et al., "Color M-mode Doppler flow propagation velocity is a relatively preload-independent index of left ventricular filling.", J Am Soc Echocardiogr. 1999 February; 12(2): 129-37.

Voller H., et al., "Acute alterations of pre- and afterload: are Doppler-derived diastolic filling patterns able to differentiate the loading condition?", Int J Card Imaging. 1993 December; 9(4):231-40.

Takahashi T., et al., "Doppler echocardiographic-determined changes in left ventricular diastolic filling flow velocity during the lower body positive and negative pressure method.", Am J Cardiol. 1990 January; 65(3):237-41.

Pela G, et al., "Effects of the reduction of preload on left and right ventricular myocardial velocities analyzed by Doppler tissue echocardiography in healthy subjects.", Eur J Echocardiogr. 2004 August; 5(4):262-71.

Kmetzo J J, et al., "Effect of postural changes and isometric exercise on Doppler-derived measurements of diastolic function in normal subjects.", Chest. 1991 August; 100(2): 357-63.

Tanabe M., et al., "Change in filling pattern with preload reduction reflects left ventricular relaxation", Intern. J. Cardiology. 2005 January; (98):67-72.

Thomas J D, et al., "Analysis of the Early Transmitral Doppler Velocity Curve: Effect of Primary Physiologic Changes and Compensatory Preload Adjustment", JACC: 1990 September; 16(3); 644-55.

Paelinck B P, et al., "Effects of Postural Changes on Cardiac Function in Healthy Subjects", Eur J Echocardiography: 2003; 4: 196-201.

Yalcin F., et al., "Is Doppler tissue velocity during early left ventricular filling preload independent?", Heart: 2002; 87:336-339.

Downes T R, et al., "Effect of Alteration in Loading Conditions on Both Normal and Abnormal Patterns of Left Ventricular Filling in Healthy Individuals", Am J Cardiology: 1990; 65:377-382.

Pepi M., et al., "Diastolic Ventricular Interaction in Normal and Dilated Heart During Head-Up Tilting", Clin Cardiology: 2000; 23:665-672

H. Suga et al., "Load Independence of the Instantaneous Pressure-Volume Ratio of the Canine Left Ventricle and Effects of Epinephrine and Heart Rate on the Ratio.", Circ Res: 1973 32: 314-322

K. Sagawa et al., "End-systolic pressure-volume ratio: a new index of ventricular contractility.", Am J Cardiol 1977 November; 40(5):748-53.

B. Oommen et al., "Modeling Time Varying Elastance: The Meaning of "Load-Independence"", Cardiovascular Engineering: 2003; 3(4): 123-130

S. J. Kovács et al., "Can Transmitral Doppler E-waves Differentiate Hypertensive Hearts From Normal?" Hypertension. 1997 October; 30(4); 788-95

C P Appleton et al., "Doppler Evaluation of Left and Right Ventricular Diastolic Function: a Technical Guide for Obtaining Optimal Flow Velocity Recordings." J Am Soc Echocardiogr. 1997 April; 10(3):271-92

C P Appleton et al. "The Echo-Doppler Evaluation of Left Ventricular Diastolic Function: a Current Perspective. In:

Diastolic Function and Dysfunction, edited by Kovács S J. Philadelphia, Pa.: Saunders, 2000; p. 513-546.

S. J. Kovács et al., "Modeling of Diastole.", Cardiology Clinics of North America. 2000 August; 18(3): 459-487

S. J. Kovács et al., "Modeling cardiac fluid dynamics and diastolic function", Philosophical Transactions of the Royal Society (A): 2001; 359: 1299-1314

J. B. Lisauskas et al., "The relation of the peak doppler E-wave to peak mitral annulus velocity ratio to diastolic function.", Ultrasound in Medicine and Biology. 2001 April; 27(4): 499-507.

A. F. Hall and S. J. Kovács Jr., "Automated method for characterization of diastolic transmitral Doppler velocity contours: Early rapid filling", Ultrasound in Medicine & Biology. 1994; 20:107-116.

A. F. Hall et al., "Automated method for characterization of diastolic transmitral Doppler velocity contours: Late atrial filling", Ultrasound in Medicine & Biology: 1994; 20: 859-869.

A. F. Hall and S. J. Kovács Jr., "Model-Based Image Processing Of Doppler Velocity Profiles Toward Automation", IEEE Ultrasonics, Ferroelectrics and Frequency Control Conference Proceedings, Seattle Wash. 1995.

S. J. Kovács Jr. et al., "Evaluation of Diastolic Function with Doppler Echocardiography: The PDF Formalism", American Journal of Physiology: 1987 January; 252(1 Pt 2):H178-H187.

H. L. Granzier and S. Labeit, "The giant protein titin: a major player in myocardial mechanics, signaling, and disease", Circ Res. 2004; 94(3): 284-295.

T. F. Robinson et al., "The heart as a suction pump", Sci Am: 1986; 254: 84-91.

J. B. Lisauskas et al. "Chamber properties from transmitral flow: prediction of average and passive left ventricular diastolic stiffness." J Appl Physiol: 2001 July; 91(1): 154-162.

L Bauman et al. "The peak atrioventricular pressure gradient to transmitral flow relation: kinematic model prediction with in-vivo validation." J Am Soc Echocardiogr: 2004 August; 17(8):839-844.

C. L. Dent et al. "Echocardiographic characterization of fundamental mechanisms of abnormal diastolic filling in diabetic rats with a parameterized diastolic filling formalism." J Am Soc Echocardiogr: 2001 December; 14(12):1166-1172

M. M. Riordan et al. "Diabetes and Diastolic Dysfunction: Stiffness and relaxation from transmitral flow." Ultrasound in Med. & Biol.: 2005 December; 31(12): 1589-1596.

L. Shmuylovich and S. J. Kovács, "A load independent index of diastolic filling: model-based derivation with in-vivo validation in control and diastolic dysfunction subjects." J Appl Physiol. 2006 July; 101(1):92-101.

A. F. Hall and S. J. Kovács Jr., "Automated Quantification of Diastolic Filling Parameters from Cardiac Doppler Ultrasound", Proceedings, 1992 IEEE Ultrasonics Symposium, October: 1125-1128, Tucson, Ariz.

Hall and S. J. Kovács Jr., "Processing parameter effects on the robustness of the solution to the "Inverse Problem" of diastole from Doppler echocardiographic data", 15th Annual International Conference, IEEE Engineering in Medicine & Biology Society: 1993; 1385-387

Lin S K et al. "Color M-Mode Flow Propagation Velocity: Is It Really Preload Independent?" Echocardiography: 2005 September; 22(8):636-641.

Kuecherer H F et al. "Determination of left ventricular filling parameters by pulsed Doppler echocardiography: a noninvasive method to predict high filling pressures in patients with coronary artery disease.", Am Heart J: 1988, 116: 1017-1021.

Stork T V et al. "Noninvasive measurement of left ventricular filling pressures by means of transmitral pulsed Doppler ultrasound.", Am J Cardiol: 1989, 64:655-660.

Kuecherer H F et al. "Estimation of mean left atrial pressure from transesophageal pulsed Doppler echocardiography of pulmonary venous flow.", Circulation: 1990, 82:1127-1139.

Mulvagh S et al. "Estimation of left ventricular end-diastolic pressure from Doppler transmitral flow velocity in cardiac patients independent of systolic performance.", J Am Coll Cardiol: 1992, 20:112-119.

Appleton C P et al. "Estimation of left ventricular filling pressures using two-dimensional and Doppler echocardiography in adult patients with cardiac disease. Additional value of analyzing left atrial size, left atrial ejection fraction and the difference in duration of pulmonary venous and mitral flow velocity at atrial contraction.", J Am Coll Cardiol: 1993, 22:1972-1982.

Vanoverschelde J L et al. "Noninvasive estimation of pulmonary arterial wedge pressure with Doppler transmitral flow velocity pattern in patients with known heart disease.", Am J Cardiol: 1995, 75:383-389.

Nishimura R A et al. "Noninvasive Doppler echocardiographic evaluation of left ventricular filling pressures in patients with cardiomyopathies: a simultaneous Doppler echocardiographic and cardiac catheterization study.", J Am Coll Cardiol: 1996, 28:1226-1233.

Pozzoli M et al. "Doppler echocardiography reliably predicts pulmonary artery wedge pressure in patients with chronic heart failure with and without mitral regurgitation.", J Am Coll Cardiol: 1996, 27:883-893.

Garcia M J et al "An index of early lefty ventricular filling that combined with pulsed Doppler peak E velocity may estimate capillary wedge pressure.", J Am Coll Cardiol: 1997, 29:448-454.

Nagueh S F et al. "Doppler tissue imaging: a noninvasive technique for evaluation of left ventricular relaxation and estimation of filling pressures.", J Am Coll Cardiol: 1997, 30:1527-1533.

Yamamoto K et al. "Determination of left ventricular filling pressure by Doppler echocardiography in patients with coronary artery disease: critical role of left ventricular systolic function.", J Am Coll Cardiol: 1997, 30:1819-1826.

Nagueh S F et al. "Doppler estimation of left ventricular filling pressure in sinus tachycardia. A new application of tissue Doppler imaging.", Circulation: 1998, 98:1644-1650.

Nagueh S F et al. "Doppler estimation of left ventricular filling pressures in patients with hypertrophic cardiomyopathy.", Circulation: 1999, 99:254-261.

Ommen S R et al. "Clinical utility of Doppler echocardiography and tissue Doppler imaging in the estimation of left ventricular filling pressures: A comparative simultaneous Doppler-catheterization study.", Circulation: 2000, 102: 1788-1794.

Dagdelen S et al. "Estimation of left ventricular end-diastolic pressure by color M-mode Doppler echocardiography and tissue Doppler imaging.", J Am Soc Echocardiogr: 2001, 14:951-958.

Kidawa M et al. "Comparative value of tissue Doppler imaging and m-mode color Doppler mitral flow propagation velocity for the evaluation of left ventricular filling pressure.", Chest: 2005, 128:2544-2550.

What is claimed is:

1. A method for obtaining an index of cardiac function comprising:
    obtaining, using computer readable code embodied on a non-transitory computer readable medium, imaging data representative of diastolic transmitral flow velocity or tissue motion in a subject at varying loads; and
    analyzing, using the computer readable code, said imaging data to determine a load-independent index of diastolic function in the subject, the load-independent index being based on a function derived from the imaging data at varying loads.

2. The method of claim 1 wherein said imaging data is obtained using a non-invasive imaging modality.

3. The method of claim 2 wherein said imaging data is obtained using an echocardiogram.

4. A method in accordance with claim 1 wherein analyzing said imaging data comprises:
    identifying a set of E-waves representing varying load states in said imaging data;
    determining values of peak-resistive force from said E-waves;
    determining values of peak-driving force from said E-waves;
    determining a linear function describing a relationship of peak driving force versus peak-resistive force for the set of E-waves;
    determining a slope of said function of maximum driving force versus peak resistive force; and
    determining the vertical intercept of said function of maximum driving force versus peak resistive force.

5. A method in accordance with claim 1 wherein analyzing said imaging data comprises:
    identifying a set of E-waves representing varying load states in said imaging data and approximating their shape as a triangle or equivalently smoothed contour;
    determining values for the acceleration times of the E-waves (AT) from said E-waves;
    determining values for the deceleration times of the E-waves (DT) from said E-waves;
    determining values for peak velocity of the E-waves ($E_{peak}$) from said E-waves;
    determining values for the geometric equivalent maximum driving force by calculating the ratio of $E_{peak}$ to AT for each E-wave from said E-waves;
    determining values for the geometric equivalent peak resistive force by calculating the following expression:

$$\frac{E_{peak}}{AT} \frac{DT^2 - AT^2}{(DT^2 - AT^2 + AT \cdot DT)}$$

for each E-wave from said E-waves;
    determining a linear function describing a relationship of said geometric equivalent maximum driving forces ($E_{peak}/AT$) to said geometric equivalent peak resistive forces $$\frac{E_{peak}}{AT} \frac{DT^2 - AT^2}{(DT^2 - AT^2 + AT \cdot DT)}$$

for all the E-waves;
    determining a slope of said function of geometric equivalent maximum driving force versus geometric equivalent peak resistive force; and
    determining a vertical intercept of said function of geometric equivalent maximum driving force versus geometric equivalent peak resistive force.

6. A method in accordance with claim 1 wherein analyzing said imaging data comprises:
    identifying a set of E-waves representing varying load states in said imaging data and approximating their shape as a triangle or equivalently smoothed contour;
    determining values for the acceleration times of the E-waves (AT) from said E-waves;
    determining values for the deceleration times of the E-waves (DT) from said E-waves;
    determining values for the peak velocity of the E-waves ($E_{peak}$) from said E-waves;
    determining values for the velocity at time t=AT/2 of the E-waves ($E_{AT/2}$) from said E-waves;
    determining values for the velocity at time t=2AT of the E-waves ($E_{2AT}$) from said E-waves;
    determining values for the geometric equivalent maximum driving force by calculating the ratio of $2E_{AT/2}$ to AT for each E-wave from said E-waves, or by determining the maximum initial upslope of the E-wave $E_{max\ initial\ upslope}$ for each E-wave from said E-waves;
    determining values for the geometric equivalent peak resistive force by calculating the following expression:

$$\frac{4E_{AT/2} \cdot DT}{(DT^2 - AT^2 + AT \cdot DT)} \frac{E_{2AT}}{E_{peak} - E_{2AT}},$$

or more generally determining values for the geometric equivalent peak resistive force calculating the following expression:

$$E_{peak} \frac{AT \cdot E_{2AT}}{E_{peak} - E_{2AT}} (E_{max\ initial\ upslope}) \frac{DT^2 - AT^2}{DT^2 - AT^2 + AT}$$

for each E-wave from said E-waves;
    determining a linear function describing a relationship of said geometric equivalent maximum driving forces ($2E_{AT/2}/AT$) to said geometric equivalent peak resistive forces $$\frac{E_{peak}}{AT} \frac{DT^2 - AT^2}{(DT^2 - AT^2 + AT \cdot DT)}$$

for all the E-waves, or more generally, determining a linear function describing a relationship of said equivalent maximum driving forces ($E_{max\ initial\ upslope}$) to said geometric equivalent peak resistive forces $$E_{peak} \frac{AT \cdot E_{2AT}}{E_{peak} - E_{2AT}} (E_{max\ initial\ upslope}) \frac{DT^2 - AT^2}{DT^2 - AT^2 + AT}$$

for all the E-waves;
    determining a slope of said function of geometric equivalent maximum driving force versus geometric equivalent peak resistive force; and
    determining a vertical intercept of said function of geometric equivalent maximum driving force versus geometric equivalent peak resistive force.

7. A method for measuring cardiac function comprising:
determining a value of a spring constant k of a spring representative of chamber recoil at varying load states;
determining a value of a chamber viscoelastic damping constant c at varying load states;
determining a value of an initial displacement of the spring $x_0$ at varying load states;
using the values of said spring constants k, the values of said damping constants c, and the values of said initial displacements of the spring $x_0$ to calculate a load independent index of diastolic function using computer readable code embodied on a non-transitory computer readable medium, wherein said spring constant k, said damping constant c, and said initial displacement of the spring $x_0$ are determined from a set of E-waves identified in imaging data representative of diastolic transmitral blood flow velocity at varying load states or of tissue motion at varying load states, and wherein the load independent index is based on a function derived from the imaging data at varying load states.

8. A system for analyzing cardiac function in a subject, said system comprising a non-transitory computer usable medium comprising:
computer readable code embodied therein, said computer readable code configured to receive an input of imaging data representative of diastolic transmitral flow at various load states or tissue motion velocity at various load states in a subject, said computer readable code further configured to generate a load-independent index of diastolic function in the subject from said imaging data, the load-independent index being based on a function derived from the imaging data at various load states.

9. A system in accordance with claim 8 further comprising:
a computer configured to operate using said computer usable medium;
display apparatus operatively coupled to said computer, said display apparatus for displaying said imaging data and said load-independent index of diastolic function.

10. A system in accordance with claim 8 wherein said computer readable code comprises:
computer readable code configured to identify a set of waves in said imaging data;
computer readable code configured to determine values of peak resistive force from said E-waves;
computer readable code configured to determine values of peak-driving force from said E-waves;
computer readable code configured to generate a linear function describing a relationship of maximum driving force versus peak resistive force for said E-waves; and
computer readable code configured to determine a slope of said function of maximum driving force versus peak resistive force; computer readable code configured to determine a vertical intercept of said function of maximum driving force versus peak resistive force.

11. A system in accordance with claim 8 wherein said computer readable code comprises:
computer readable code configured to identify a set of E-waves in said imaging data;
computer readable code configured to determine values for the acceleration times of the E-waves (AT) from said E-waves;
computer readable code configured to determine values for the deceleration times of the E-waves (DT) from said E-waves;
computer readable code configured to determine values for the peak velocity of the E-waves ($E_{peak}$) from said E-waves;
computer readable code configured to determine values for the geometric equivalent maximum driving force by calculating the ratio of $E_{peak}$ to AT for each E-wave from said E-waves;
computer readable code configured to determine values for the geometric equivalent peak resistive force by calculating the following expression:

$$\frac{E_{peak}}{AT} \frac{DT^2 - AT^2}{(DT^2 - AT^2 + AT \cdot DT)}$$

for each E-wave from said E-waves;
computer readable code configured to determine a linear function describing a relationship of said geometric equivalent maximum driving forces ($E_{peak}$/AT) to said geometric equivalent peak resistive forces $$\frac{E_{peak}}{AT} \frac{DT^2 - AT^2}{(DT^2 - AT^2 + AT \cdot DT)}$$

for all the E-waves;
computer readable code configured to determine a slope of said function of geometric equivalent maximum driving force versus geometric equivalent peak resistive force;
and computer readable code configured to determine a vertical intercept of said function of geometric equivalent maximum driving force versus geometric equivalent peak resistive force.

12. A system in accordance with claim 8 wherein said computer readable code comprises:
computer readable code configured to identify a set of E-waves in said imaging data;
computer readable code configured to determine values for the acceleration times of the E-waves (AT) from said E-waves;
computer readable code configured to determine values for the deceleration times of the E-waves (DT) from said E-waves;
computer readable code configured to determine values for the peak velocity of the E-waves ($E_{peak}$) from said E-waves;
computer readable code configured to determine values for the velocity at time t=AT/2 of the E-waves ($E_{AT/2}$) from said E-waves;
computer readable code configured to determine values for the velocity at time t=2AT of the E-waves ($E_{2AT}$) from said E-waves;
computer readable code configured to determine values for the geometric equivalent maximum driving force by calculating the ratio of $2E_{AT/2}$ to AT for each E-wave from said E-waves, or computer readable code configured to determine the maximum initial upslope of the E-wave $E_{max\ initial\ upslope}$ for each E-wave from said E-waves;
computer readable code configured to determine the geometric equivalent peak resistive force by calculating the following expression:

$$E_{peak} \frac{AT \cdot E_{2AT}}{E_{peak} - E_{2AT}} (E_{max\ initial\ upslope}) \frac{DT^2 - AT^2}{DT^2 - AT^2 + AT}$$

for each E-wave from said E-waves;
computer readable code configured to determine a linear function describing a relationship of said equivalent maximum driving forces ($E_{max\ initial\ upslope}$) to said geometric equivalent peak resistive forces $$E_{peak} \frac{AT \cdot E_{2AT}}{E_{peak} - E_{2AT}} (E_{max\ initial\ upslope}) \frac{DT^2 - AT^2}{DT^2 - AT^2 + AT}$$

for all the E-waves;
computer readable code configured to determine a slope of said function of geometric equivalent maximum driving force versus geometric equivalent peak resistive force; and computer readable code configured to determine a vertical intercept of said function of geometric equivalent maximum driving force versus geometric equivalent peak resistive force.

13. A system in accordance with claim 8 wherein said computer readable code comprises:
computer readable code configured to identify a set of E-waves in said imaging data;
computer readable code configured to determine from each said E-wave a value of a spring constant k of a spring representative of chamber recoil;
computer readable code configured to determine from each said E-wave a value of a chamber viscoelastic damping constant c;
computer readable code configured to determine from each said E-wave a value of an initial displacement of the spring $x_0$;
computer readable code configured to use the values of said spring constants k, the values of said damping constants c, and the values of said initial displacements of the spring $x_0$ to calculate a load independent index of diastolic function.

14. Apparatus for displaying indices of cardiac function in a subject, said apparatus comprising:
a non-transitory computer usable medium comprising computer readable code embodied therein, said computer readable code configured to receive an input of imaging data representative of diastolic transmitral flow velocity at varying loads or tissue motion at varying loads in a subject, said computer readable code further configured to generate a load-independent index of diastolic function in the subject from said imaging data, the load-independent index being based on a function derived from the imaging data at varying loads; and
a visual display apparatus operatively coupled to said computer usable medium, said visual display apparatus configured to display said imaging data and said load-independent index of diastolic function.

15. A diagnostic system for analyzing cardiac function in a subject, said system comprising:
a computer processor, said computer processor configured with computer readable instructions comprising:
instructions for receiving and storing an input of imaging data representative of diastolic transmitral flow velocity at varying loads in a subject; and
instructions for generating a load-independent index of diastolic function in the subject from said imaging data, the load-independent index being based on a function derived from the imaging data at varying loads.

16. A diagnostic system in accordance with claim 15 wherein said computer readable instructions further comprise:
instructions for identifying a set of E-waves in said imaging data;
instructions for determining values of peak resistive force from said E-waves;
instructions for determining values of maximum driving force from said E-waves;
instructions for generating a linear function describing a relationship of maximum driving force versus peak resistive force; and
instructions for determining a slope and vertical intercept of said function of maximum driving force versus peak resistive force.

17. A diagnostic system in accordance with claim 15 wherein said computer readable instructions further comprise:
instructions for identifying a set of E-waves in said imaging data; instructions for determining values for the acceleration time of each E-wave (AT) from said E-waves;
instructions for determining values for the deceleration time of each E-wave (DT) from said E-waves;
instructions for determining values for the peak velocity of each E-waves ($E_{peak}$) from said E-waves;
instructions for determining values for the geometric equivalent maximum driving force by calculating the ratio of $E_{peak}$ to AT for each E-wave from said E-waves;
instructions for determining values for the geometric equivalent peak resistive force by calculating the following expression:

$$\frac{E_{peak}}{AT} \frac{DT^2 - AT^2}{(DT^2 - AT^2 + AT \cdot DT)}$$

for each E-wave from said E-waves;
instructions for determining a linear function describing a relationship of said geometric equivalent maximum driving forces ($E_{peak}/AT$) to said geometric equivalent peak resistive forces $$\frac{E_{peak}}{AT} \frac{DT^2 - AT^2}{(DT^2 - AT^2 + AT \cdot DT)}$$

for all the E-waves;
instructions for determining a slope of said function of geometric equivalent maximum driving force versus geometric equivalent peak resistive force; and
instructions for determining a vertical intercept of said function of geometric equivalent maximum driving force versus geometric equivalent peak resistive force.

18. A diagnostic system in accordance with claim 15 wherein said computer readable instructions further comprise:
instructions for identifying a set of E-waves in said imaging data;
instructions for determining values for the acceleration times of the E-waves (AT) from said E-waves;
instructions for determining values for the deceleration times of the E-waves (DT) from said E-waves;
instructions for determining values for the peak velocity of the E-waves ($E_{peak}$) from said E-waves;
instructions for determining values for the velocity at time t=AT/2 of the E-waves ($E_{AT/2}$) from said E-waves;
instructions for determining values for the velocity at time t=2AT of the E-waves ($E_{2AT}$) from said E-waves;
instructions for determining values for the geometric equivalent maximum driving force by calculating the ratio of $2E_{AT/2}$ to AT for each E-wave from said E-waves, or instructions for determining the maximum initial upslope of the E-wave $E_{max\ initial\ upslope}$ from said E-waves;

instructions for determining the geometric equivalent peak resistive force by calculating the following expression:

$$E_{peak} \frac{AT \cdot E_{2AT}}{E_{peak} - E_{2AT}} (E_{max\ initial\ upslope}) \frac{DT^2 - AT^2}{DT^2 - AT^2 + AT}$$

for each E-wave from said E-waves;
instructions for determining a linear function describing a relationship of said equivalent maximum driving forces ($E_{max\ initial\ upslope}$) to said geometric equivalent peak resistive forces $$E_{peak} \frac{AT \cdot E_{2AT}}{E_{peak} - E_{2AT}} (E_{max\ initial\ upslope}) \frac{DT^2 - AT^2}{DT^2 - AT^2 + AT}$$

for all the E-waves;
instructions for determining a slope of said function of geometric equivalent maximum driving force versus geometric equivalent peak resistive force; and
instructions for determining a vertical intercept of said function of geometric equivalent maximum driving force versus geometric equivalent peak resistive force.

19. A diagnostic system in accordance with claim 15 wherein said computer readable instructions further comprise:
instructions for identifying a set of E-waves in said imaging data;
instructions for determining from each said E-wave a value of a spring constant k of a spring representative of chamber recoil;
instructions for determining from each said E-wave a value of a chamber viscoelastic damping constant c;
instructions for determining from each said E-wave a value of an initial displacement of the spring $x_0$;
instructions for using the values of said spring constants k, the values of said damping constants c, and the values of said initial displacements of the spring $x_0$ to calculate a load independent index of diastolic function.

* * * * *